(12) United States Patent
Hauptmann et al.

(10) Patent No.: US 10,241,418 B2
(45) Date of Patent: Mar. 26, 2019

(54) METHOD AND APPARATUS FOR OBTAINING DIAGNOSTIC INFORMATION RELATING TO A LITHOGRAPHIC MANUFACTURING PROCESS, LITHOGRAPHIC PROCESSING SYSTEM INCLUDING DIAGNOSTIC APPARATUS

(71) Applicant: ASML NETHERLANDS B.V., Veldhoven (NL)

(72) Inventors: Marc Hauptmann, Leuven (BE); Dylan John David Davies, Heeswijk-Dinter (NL); Paul Janssen, Eindhoven (NL); Naoko Tsugama, Moergestel (NL); Richard Joseph Bruls, Eindhoven (NL); Kornelis Tijmen Hoekerd, Eindhoven (NL); Edwin Johannes Maria Janssen, Helmond (NL); Petrus Johannes Van Den Oever, Eindhoven (NL); Ronald Van Der Wilk, Knegsel (NL); Antonius Hubertus Van Schijndel, Deurne (NL); Jorge Alberto Vieyra Salas, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/527,645

(22) PCT Filed: Sep. 21, 2015

(86) PCT No.: PCT/EP2015/071600
§ 371 (c)(1),
(2) Date: May 17, 2017

(87) PCT Pub. No.: WO2016/087069
PCT Pub. Date: Jun. 9, 2016

(65) Prior Publication Data
US 2017/0363969 A1    Dec. 21, 2017

(30) Foreign Application Priority Data

Dec. 1, 2014   (EP) ..................................... 14195683

(51) Int. Cl.
*G03B 27/52* (2006.01)
*G03B 27/42* (2006.01)
(Continued)

(52) U.S. Cl.
CPC ..... *G03F 7/70616* (2013.01); *G01N 21/9501* (2013.01); *G03F 1/84* (2013.01);
(Continued)

(58) Field of Classification Search
CPC .. G01N 21/956; G01N 21/4795; G01N 21/94; G01N 2021/4709; G01N 21/3563;
(Continued)

(56) References Cited

U.S. PATENT DOCUMENTS 7,130,036 B1   10/2006   Kuhlmann et al.
7,227,628 B1    6/2007   Sullivan et al.
(Continued)

FOREIGN PATENT DOCUMENTS

JP    1993-241415    9/1993

OTHER PUBLICATIONS

International Search Report and Written Opinion dated Apr. 19, 2016 in corresponding International Patent Application No. PCT/EP2015/071600.
(Continued)

*Primary Examiner* — Mesfin T Asfaw
(74) *Attorney, Agent, or Firm* — Pillsbury Winthrop Shaw Pittman LLP

(57) ABSTRACT

A diagnostic apparatus monitors a lithographic manufacturing system. First measurement data representing local deviations of some characteristic across a substrate is obtained
(Continued)

using sensors within a lithographic apparatus, and/or a separate metrology tool. Other inspection tools perform substrate backside inspection to produce second measurement data. A high-resolution backside defect image is processed into a form in which it can be compared with lower resolution information from the first measurement data. Cross-correlation is performed to identify which of the observed defects are correlated spatially with the deviations represented in the first measurement data. A correlation map is used to identify potentially relevant clusters of defects in the more detailed original defect map. The responsible apparatus can be identified by pattern recognition as part of an automated root cause analysis. Alternatively, reticle inspection data may be used as second measurement data.

20 Claims, 10 Drawing Sheets

(51) Int. Cl.
  G03F 7/20          (2006.01)
  G03F 1/84          (2012.01)
  G01N 21/95         (2006.01)
  H01L 21/66         (2006.01)
  G01N 21/956        (2006.01)
  G01N 27/61         (2006.01)

(52) U.S. Cl.
  CPC ...... *G03F 7/70508* (2013.01); *G03F 7/70783* (2013.01); *G01N 27/61* (2013.01); *G01N 2021/95676* (2013.01); *H01L 22/12* (2013.01); *H01L 22/20* (2013.01)

(58) Field of Classification Search
  CPC ........... G01N 21/8851; G01N 21/9505; G01N 2021/4733; G01N 21/88; G01N 21/95607; G01N 21/95623; G01N 2021/8887; G01N 21/892; G01N 2223/401; G01N 2223/418; G01N 2223/646
  See application file for complete search history.

(56) References Cited

U.S. PATENT DOCUMENTS

| | | |
|---|---|---|
| 7,968,354 B1 | 6/2011 | Haller et al. |
| 2005/0038554 A1 | 2/2005 | Watkins |
| 2015/0211836 A1 | 7/2015 | Devilliers et al. |

OTHER PUBLICATIONS

Carlson, Alan et al., "Correlation of Wafer Backside Defects to Photolithography Hot Spots Using Advanced Macro Inspection", Proceedings of SPIE, vol. 6152, pp. 61523E1-61523E7 (2006).
Huttenlocher, D. P. et al., "Comparing Images Using the Hausdorff Distance", IEEE Transactions on Pattern Analysis and Machine Intelligence, vol. 15, No. 9, pp. 850-863 (1993).
Dubuisson, Marie-Pierre et al., "A Modified Hausdorff Distance for Object Matching", Proc. International Conference on Pattern Recognition, pp. 566-568 (1994).
Belongie, Serge et al., "Shape Matching and Object Recognition Using Shape Contexts" IEEE Transactions on Pattern Analysis and Machine Intelligence, vol. 24, No. 24, pp. 509-522 (2002).
Lederer, K. et al., "Wafer backside inspection applications in lithography", 2003 Proceedings IEEE/Semi Advanced Semiconductor Manufacturing Conference, 8 pages (2003).
Raghunathan, Sudhar et al., "Correlation of overlay performance and reticle substrate non-flatness effects in EUV lithography", Proceedings of SPIE, vol. 7488, pp. 748816-1-748816-9 (2009).
Korean Office Action issued in corresponding Korean Patent Application No. 10-2017-7017245, dated Sep. 6, 2018.

METHOD AND APPARATUS FOR OBTAINING DIAGNOSTIC INFORMATION RELATING TO A LITHOGRAPHIC MANUFACTURING PROCESS, LITHOGRAPHIC PROCESSING SYSTEM INCLUDING DIAGNOSTIC APPARATUS

CROSS REFERENCE TO RELATED APPLICATIONS

This application is the U.S. national phase entry of PCT patent application No. PCT/EP2015/071600, which was filed on Sep. 21, 2015, which claims the benefit of priority of European patent EP application No. 14195683.9, which was filed on Dec. 1, 2014 and which is incorporated herein in its entirety by reference.

BACKGROUND

Field of the Invention

The invention relates to a diagnostic apparatus for use in an industrial process. An example of an industrial process for which the apparatus has been developed is a lithographic manufacturing process, which includes one or more steps of transferring a pattern from a patterning device onto a substrate using a lithographic apparatus.

Related Art

A lithographic process is a manufacturing process in which the lithographic apparatus applies a desired pattern onto a substrate, usually onto a target portion of the substrate. The patterning step performed by the lithographic apparatus is just one step in a sequence of processing steps performed on each substrate in the entire lithographic process. The processing steps generally including one or more pre-patterning process steps and one or more post-patterning process steps. Examples of pre-patterning steps include steps for applying or modifying layers of product material or mask material, applying a base anti-reflection coating (BARC) and applying a radiation-sensitive resist. Examples of post-patterning process steps include developing the resist, etching a product material or mask material in accordance with the pattern, removing resist, cleaning and so forth. Each substrate may pass through many cycles of patterning steps and processing steps, to build up a desired product structure. Each of the steps involves one or more handling operations, in addition to the chemical and/or physical processes of the steps themselves. Any of these handling operations can introduce defects to the substrate, which influence the performance of subsequent processing steps. Defects may consist of damage to the material of the substrate, or particles of contaminant material adhering to the substrate. Contamination can be transferred from a substrate to the substrate support or other handling apparatus, affecting processing of other substrates in due course.

Performance of the lithographic process can be measured by various parameters. A particular performance parameter known as overlay error or simply "overlay", relates to the ability to position successive layers of features in superposition accurately enough to produce working devices with a high yield. Overlay should, in general, be achieved within a few tens of nanometers in today's sub-micron semiconductor devices, down to a few nanometers in the most critical layers. Other performance parameters such as critical dimension (CD or line width) also should be optimized and made uniform across the substrate, to ensure good yield and performance of the manufactured devices. To achieve good performance in such parameters, the substrate should be stable and flat during the patterning step. Typically the substrate is held on a substrate support by a clamping force. Conventionally the clamping is achieved by suction. In the latest lithography tools using extreme ultraviolet (EUV) radiation, the patterning operation is conducted in a vacuum environment. In that case, the clamping force is achieved by electrostatic attraction.

Defects such as damage or contamination on the reverse side of the substrate can cause the substrate to be distorted. In particular, it will be understood that particles of contamination between the substrate and the substrate support can cause local deviations in height, either directly or because they introduce local deviations in clamping force. Some variation in height across the substrate is normally measured and corrected for in the patterning step, so as to maintain accurate focus. However, defects of the type described above can introduce very localized height deviations, in other words curvature or "unflatness" of the substrate surface. These deviations are not corrected by existing control systems. As explained in more detail below, local curvature can affect not only focusing performance but also positioning (overlay) performance.

Defects on a patterning device (mask or reticle) MA, may also arise and affect performance of the lithographic process. Reticles are also subject to handling operations, as the lithographic apparatus is used to apply different patterns to different substrates, and to different layers on the same substrates. Reticles are therefore subject to damage and contamination in the same way as the substrates to which the pattern is to be applied. Reticles are also held by suction and/or electrostatic clamping force during the patterning step. Distortion especially local curvature in the reticle can lead to loss of performance in overlay, CD etc. in the same way as local curvature of the substrate.

Consequently, a major problem for operators of lithographic manufacturing facilities is to detect and eliminate contamination or other defects as they affect yield. On the other hand, to interrupt operations of the expensive equipment, whether for inspection or cleaning/replacement of parts, is extremely costly in itself. Unnecessary maintenance operations are also costly, not only because of the interruption to productive operations, but also because they may reduce the lifetime of components. Therefore the operator would want to know not only whether observed performance issues are caused by defects, but also which specific apparatuses and steps are the root cause of the defects and their consequent performance issues. Unfortunately, modern lithographic process and products are so complex that such issues are difficult to trace back to the root cause.

Errors in focus and/or positioning and overlay that are not corrected by measurement and control in the patterning operation can be identified. These so-called residuals typically have a spatial distribution over the substrate that may be regarded as a "fingerprint" of the process applied to the substrate so far. Naturally this process fingerprint is a combination of individual fingerprints of every processing operation and handling operation that the substrate has undergone so far. Contamination may be transferred from one apparatus to another on the back off one or more substrates. The analysis required to discover where such damage or contamination lies and/or where it originates can therefore be time consuming and difficult. An expert may, by visual inspection and detailed analysis of the distribution, give an indication of possible causes and strategies for investigation and correction. However, a typical defect map will show many features and most of these will not necessarily relate to detrimental effects in performance. Also, to subject substrates to such inspection is costly and disruptive in itself, and may not be helpful if one does not know what one is looking for.

Some measurements are relatively easy and quick to obtain, but can make classifying the source of contamination difficult. As an example, one can use height map data from measurements that are routinely made as part of the patterning step. This data obtained as a by-product of the patterning step, with little or no impact on throughput can be termed 'inline' data. The same applies to measurements of performance parameters such as overlay or CD that may be made after patterning. Direct inspection of the wafer (or reticle) reverse side allows detailed mapping of defects. However, this data is not necessarily available without significant measurement overhead. It may be termed 'offline' data, as it is obtained separately from the routine handling. Further, the sheer volume of information that may be obtained by offline inspection that diagnosis of root causes and determination of appropriate corrective action relies on making a careful choice of defects to investigate. Linking inline measurements on a substrate or reticle with offline defect inspection measurements is more effective. However, it is typically done by hand, by experts who carry out defect review sampling. It may therefore take some time before appropriate action can be taken to counteract the contamination. In a worst-case scenario, unplanned downtime may be required to deal with serious incidences of backside contamination.

SUMMARY OF THE INVENTION

The present invention in a first aspect provides a diagnostic apparatus for use in relation to a lithographic process, the diagnostic apparatus comprising a data processing apparatus programmed to perform automatically the steps of:

receiving first measurement data representing a distribution of local deviations of a characteristic of one or more substrates subjected to the lithographic process; receiving second measurement data, the second measurement data representing a distribution of defects observed either on one or more substrates subjected to the same lithographic process or on a patterning device from which a pattern is transferred to said substrates in a patterning step of the lithographic process; identifying a correlation between the distribution of defects represented in the second measurement data and the distribution of local deviations represented in the first measurement data; and generating diagnostic information relating to the lithographic process based on the identified correlation.

By finding correlations between different types of measured data, the apparatus can automatically obtain diagnostic information much more quickly than the existing methods. The availability of this diagnostic information can allow better planning of maintenance operations to maximize yield and productivity. Where there is actually a need for an urgent intervention, this can be identified much more quickly. At the same time, unnecessary interventions for inspection and/or maintenance can be avoided, reducing downtime and extending component lifetimes. For example, early warning of contamination issues may allow certain maintenance operations to be brought forward into scheduled downtime rather than waiting until there is an emergency.

In some embodiments, the distribution of the first measurement data represents distribution of local deviations with a first spatial resolution and the second measurement data represents the distribution of defects with a second spatial resolution, the second spatial resolution being higher than the first spatial resolution. For example, the apparatus may be operable to use relatively low-resolution data such as may be obtained by routine measurement within the lithographic tool (patterning apparatus) and/or routine performance monitoring, with higher resolution data such as may be obtained by direct inspection of the wafer backside. The second measurement data may be converted to a form having the same spatial resolution as the first measurement data for the step of identifying correlations.

In some embodiments, portions of the higher resolution second measurement data are then retrieved for use in obtaining the diagnostic information. In this way, the correlation result can be used to select which portions of the high resolution data contain likely clues as to the source of significant defects. For example, the apparatus may be arranged to identify clusters of defects in the second measurement data. The correlation result can be used to select clusters that fall into regions of identified correlation.

The first measurement data may for example be based on height map data representing local deviations of surface height as a characteristic of the substrate. Some height map data is generally measured for a patterning step of said lithographic process. The height map data may be used to derive curvature (local curvature) information for use as the first measurement data.

In a particular embodiment, the first measurement data is based on first and second height map data measured with the substrate subjected to different clamping conditions on the substrate support. This allows additional diagnostic information to be obtained. The different clamping conditions may comprise different magnitudes of clamping force, and/or different polarities of clamping voltage on an electrostatic substrate support.

The first measurement data may be obtained by comparing height map data (either in a raw or processed form) measured from a first substrate with reference height map data measured previously from one or more reference substrates, the reference substrates being regarded as free of defects. Reference data may alternatively be obtained by filtering data from the substrate or substrates being measured. It should be understood that this does not require that the raw height map data from the substrate and the reference substrate should be compared directly. The height map data may be processed into some derivative form, such as a map of curvature, before being compared.

Alternatively or in addition, the first measurement data may include data measured by the patterning apparatus from a substrate support after the first substrate has been removed from the substrate support after said patterning step. For example the first measurement data in this situation may include measurements of electrostatic voltage variations across the substrate support.

Alternatively or in addition, the first measurement data may include measurements of one or more performance parameters of the patterns applied to the substrate in said patterning step measured on a front side of the substrate by an inspection apparatus, for example an optical inspection apparatus such as a microscope or a scatterometer, an electron microscope or the like.

In this situation, said performance parameter may be for example overlay or critical dimension.

In an embodiment, the processor is further provided with a database of defect fingerprints, each defect fingerprint representing a spatial distribution of defects associated with one or more specific handling operations in the lithographic process, and the step of generating diagnostic information includes recognizing from the identified correlation, which, if any, of the defect fingerprints matches a spatial distribution of defects in the second measurement data correlated with the distribution of local deviations represented in the first measurement data.

The processor may be arranged to recognize which of the defect fingerprints matches the spatial distribution of defects map by calculating a frequency spectrum of distances between defects in the identified regions.

In an embodiment, the processor is arranged to identify said correlation by: deriving from the first measurement data a deviation map representing a distribution of local deviations in multiple regions distributed spatially across the substrate; and deriving from the second measurement data a defect map representing a density of defects observed in regions corresponding in spatial distribution with the regions of the deviation map; and identifying regions where the density of defects in the defect map is correlated with the density of local deviations in the deviation map.

Where the second measurement data has a higher spatial resolution than the second measurement data, the processor may be arranged to produce a low resolution representation of the second measurement data for use in identifying the correlation with the first measurement data. In such an embodiment, the processor may then use the identified correlation to identify specific portions the higher resolution second measurement data, and use these for obtaining the diagnostic information.

Preferably, the apparatus is adapted for use where said lithographic process includes performing one or more of said processing steps by different individual processing apparatuses on different individual substrates, and wherein the processor is arranged to use context data identifying the individual processing apparatus used for a given processing step on the first substrate.

In another aspect, the present invention also provides a computer program product or other non-transient memory device, having stored there on software that when run on a computer causes the computer to carry out the steps of: receiving first measurement data representing a distribution of local deviations of a characteristic of one or more substrates subjected to the lithographic process; receiving second measurement data, the second measurement data representing a distribution of defects observed either on one or more substrates subjected to the same lithographic process or on a patterning device from which a pattern is transferred to said substrates in a patterning step of the lithographic process; identifying a correlation between the distribution of defects represented in the second measurement data and the distribution of local deviations represented in the first measurement data; and generating diagnostic information relating to the lithographic process based on the identified correlation.

The computer program product may further contain instructions for specifically implementing any of the optional features, described above.

BRIEF DESCRIPTION OF THE DRAWINGS

Embodiments of the invention will now be described, by way of example only, with reference to the accompanying schematic drawings in which:

FIG. 4 (*b*) shows a weighting function for normalizing the first measurement data of FIG. 4 (*a*);

FIG. 4 (*c*) shows a dimensionless weighted data plot based on the showing the first measurement data after application of the weighting function;

FIG. 4 (*d*) shows a map of substrate backside defect data for use as second measurement data in the diagnostic apparatus;

FIG. 4 (*e*) shows a summed plot of defect density for a 1-5 μm defect size range based on offline measured data;

FIG. 4 (*f*) shows a dimensionless weighting function based on a cumulative Gaussian function for use with the offline data of FIG. 4*d*;

FIG. 4 (*g*) illustrates the weighted defect density in the range 1-5 μm based on the offline measured data and the weighting function;

DETAILED DESCRIPTION OF EXEMPLARY EMBODIMENTS

Before describing the techniques that are the specific subject of the present disclosure, it will be useful to present some background information on lithographic manufacturing processes and the issues arising therein. The examples will concern primarily processes for the production of functional devices on semiconductor substrates. The same principles can be applied to other types of product or substrates. It should also be appreciated in particular that the same principles can be applied in the manufacture of patterning devices such as reticles, which may themselves be used in a subsequent manufacturing process. Accordingly, references to the substrate in what follows may be construed also as references to a substrate on which a master pattern is to be formed, this being used subsequently for the applying functional device patterns to a series of substrates.

The patterning device can be an optical lithography reticle, either transmissive or reflective in type. The patterning device may alternatively be a template for use in imprint lithography, for example.

Figure 1:
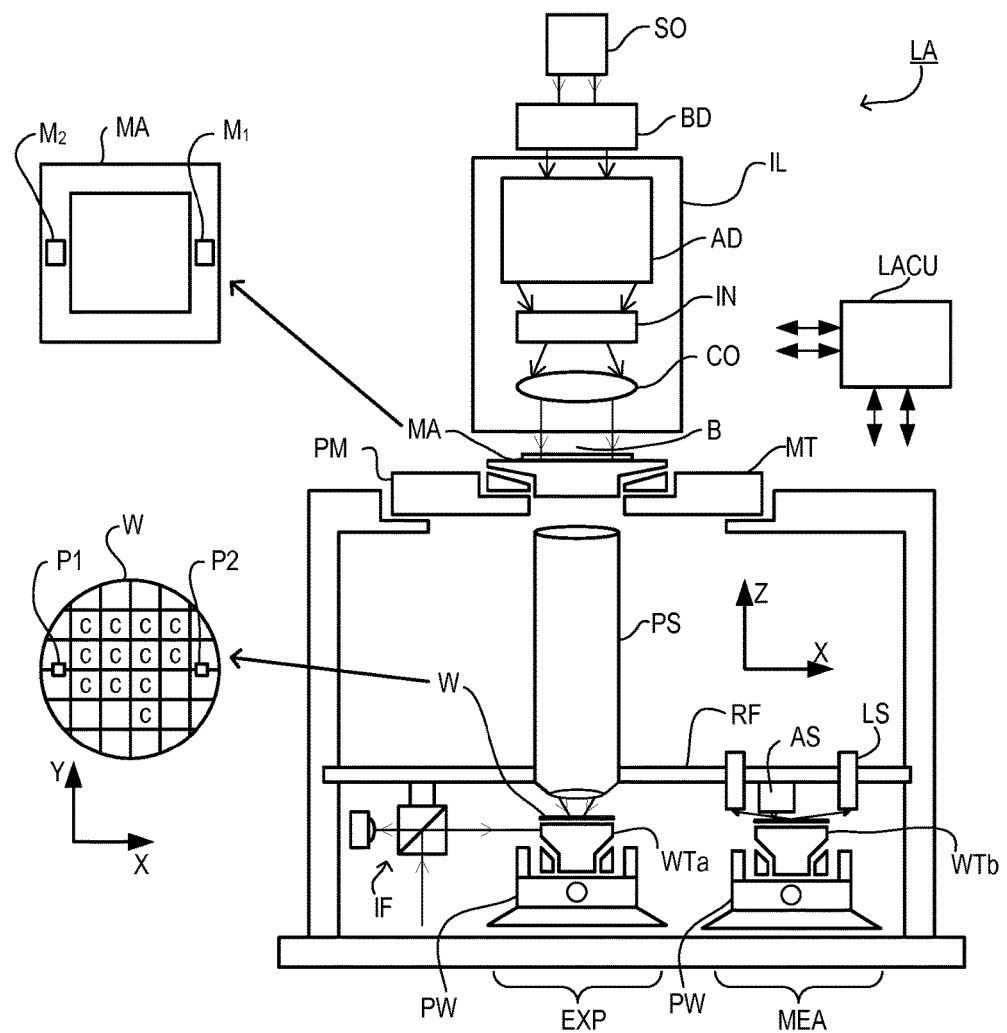
FIG. 1 depicts a lithographic apparatus according to an embodiment of the invention.

FIG. 1 schematically depicts a lithographic apparatus LA according to one embodiment of the invention. The apparatus comprises:

an illumination system (illuminator) IL configured to condition a radiation beam B (e.g. UV radiation or EUV radiation).

a support structure (e.g. a mask table) MT constructed to support a patterning device (e.g. a mask) MA and connected to a first positioner PM configured to accurately position the patterning device in accordance with certain parameters;

a substrate table (e.g. a substrate table) WTa or WTb constructed to hold a substrate (e.g. a resist-coated substrate) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W. The substrate W, or wafer, has a front side, positioned uppermost during processing, onto which the various processing steps are incident, and a backside, opposite the front side and in contact with the substrate table WTa, WTb, during processing. The backside is vulnerable to contamination that may lead to the distortion of the front side, as described below.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure. The invention disclosed herein can be used in a stand-alone fashion, but in particular it can provide additional functions in the pre-exposure measurement stage of either single- or multi-stage apparatuses.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g. an interferometric device, linear encoder or capacitive sensor), the substrate table WTa/WTb can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WTa/WTb may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WTa/WTb are kept essentially stationary, while an entire pattern imparted to the radiation beam is projected onto a target portion C at one time (i.e. a single static exposure). The substrate table WTa/WTb is then shifted in the X and/or Y direction so that a different target portion C can be exposed. In step mode, the maximum size of the exposure field limits the size of the target portion C imaged in a single static exposure.
2. In scan mode, the mask table MT and the substrate table WTa/WTb are scanned synchronously while a pattern imparted to the radiation beam is projected onto a target portion C (i.e. a single dynamic exposure). The velocity and direction of the substrate table WTa/WTb relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.
3. In another mode, the mask table MT is kept essentially stationary holding a programmable patterning device, and the substrate table WTa/WTb is moved or scanned while a pattern imparted to the radiation beam is projected onto a target portion C. In this mode, generally a pulsed radiation source is employed and the programmable patterning device is updated as required after each movement of the substrate table WTa/WTb or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA in this example is of a so-called dual stage type which has two substrate tables WTa and WTb and two stations—an exposure station and a measurement station—between which the substrate tables can be exchanged. While one substrate on one substrate table is being exposed at the exposure station EXP, another substrate can be loaded onto the other substrate table at the measurement station MEA so that various preparatory steps may be carried out. The preparatory steps may include mapping the surface height of the substrate using a level sensor LS and measuring the position of alignment marks on the substrate using an alignment sensor AS. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus LA is to print product features at the correct locations with very high accuracy. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. The invention can be applied in apparatus with only one substrate table, or with more than two.

The apparatus further includes a lithographic apparatus control unit LACU which controls all the movements and measurements of the various actuators and sensors described. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus. For example, one processing subsystem may be dedicated to servo control of the substrate positioner PW. Separate units may even handle coarse and fine actuators, or different axes. Another unit might be dedicated to the readout of the position sensor IF. Overall control of the apparatus may be controlled by a central processing unit, communicating with these sub-systems processing units, with operators and with other apparatuses involved in the lithographic manufacturing process.

Figure 2:
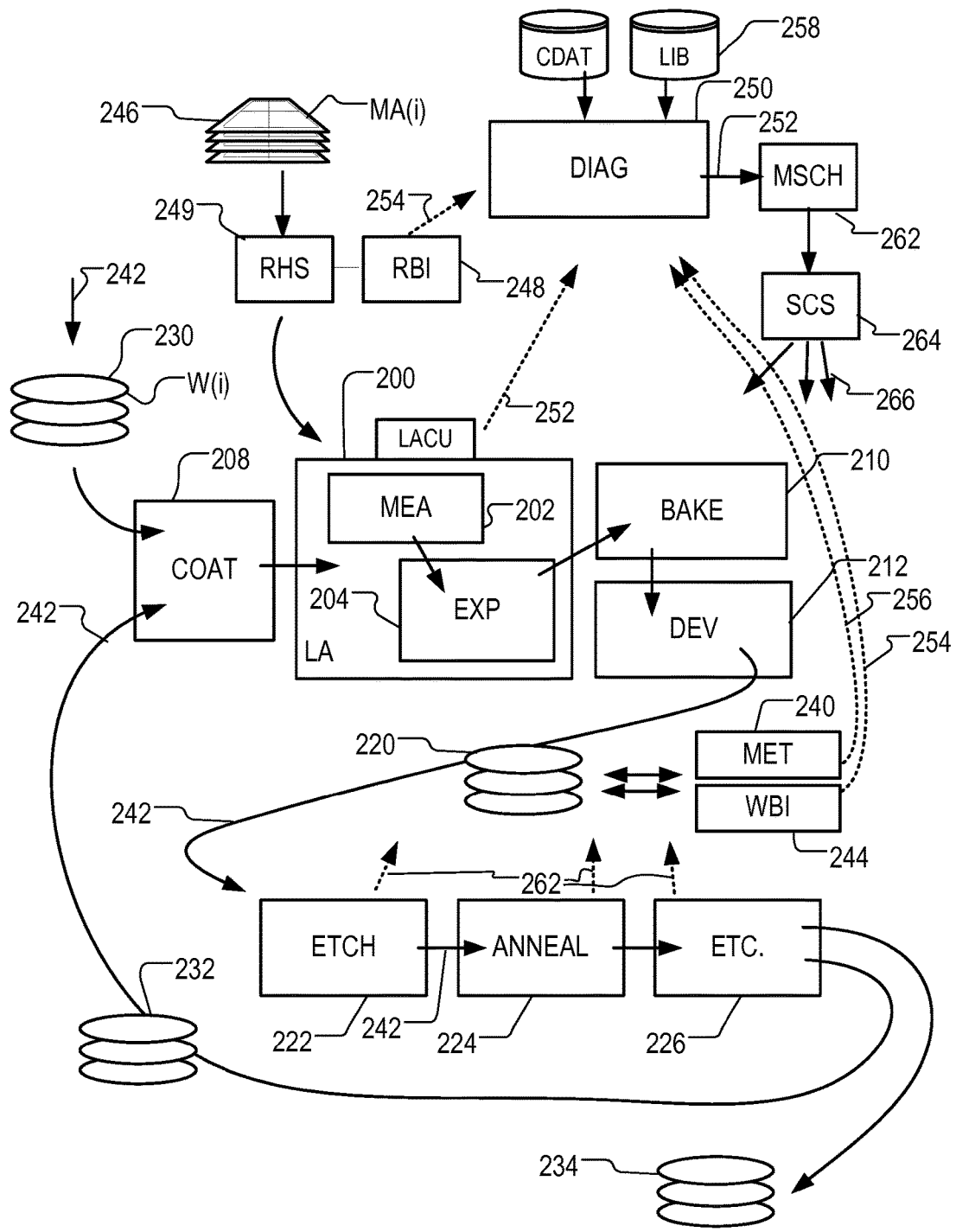
FIG. 2 shows schematically the use of the lithographic apparatus of FIG. 1 together with other apparatuses forming a lithographic production system for semiconductor devices, the system further including diagnostic apparatus according to embodiments of the present invention.

FIG. 2 at 200 shows the lithographic apparatus LA in the context of an industrial production facility for semiconductor products. Within the lithographic apparatus (or "litho tool" 200 for short), the measurement station MEA is shown at 202 and the exposure station EXP is shown at 204. The control unit LACU is shown at 206. Within the production facility, apparatus 200 forms part of a "litho cell" or "litho cluster" that contains also a coating apparatus 208 for applying photosensitive resist and other coatings to substrate W for patterning by the apparatus 200. At the output side of apparatus 200, a baking apparatus 210 and developing apparatus 212 are provided for developing the exposed pattern into a physical resist pattern.

Once the pattern has been applied and developed, patterned substrates 220 are transferred to other processing apparatuses such as are illustrated at 222, 224, 226. A wide range of processing steps are implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

Also shown in FIG. 2 is a metrology apparatus 240 which is provided for making measurements of parameters of the products at desired stages in the manufacturing process. A common example of a metrology station in a modern lithographic production facility is a scatterometer, for example an angle-resolved scatterometer or a spectroscopic scatterometer, and it may be applied to measure properties of the developed substrates at 220 prior to etching in the apparatus 222. Using metrology apparatus 240, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. As is also well known, the metrology results from the apparatus 240 can be used to maintain accurate performance of the patterning operations in the litho cluster, by making small adjustments over time, thereby minimizing the risk of products being made out-of-specification, and requiring re-work. Of course, metrology apparatus 240 and/or other metrology apparatuses (not shown) can be applied to measure properties of the processed substrates 232, 234, and incoming substrates 230.

In addition to measuring performance parameters on the patterned products, the lithographic production system may include inspection apparatus specifically for identifying defects in front and/back sides of the substrates and reticles. These defects, such as contaminant particles adhering to the substrate, can arise in any of the many handling operations that are involved in the lithographic process. Solid arrows in FIG. 2 indicate schematically these handling operations, which are performed by automated apparatus in a cleanroom environment. A few of these are labeled 242 for ease of identification. Defects can also include scratches, dents or even modifications in the material of the substrate. Inspection apparatus 240 can be used for defect inspection on a front side of the substrate, but a particular problem is in backside defects, resulting from contact with the various handling apparatuses. To inspect for these a separate backside inspection apparatus 244 is provided. Commercially available devices such as KLA-Tencor SP2 or AMAT Uvision are often used for this purpose. Not every substrate is inspected, but substrates or batches (lots) of substrates can be diverted to such inspection apparatus either on a routine sampling basis, or because specific problems have been identified. Further inspection apparatuses (not shown in FIG. 2) can be called upon, for example to apply electron microscopy or X-ray diffraction to analyze detailed structures and/or material composition. In particular, systems that combine Scanning Electron Microscopy (SEM) with Energy Dispersive X-Ray Analysis (EDX) are commercially available. In these systems, SEM provides detailed high resolution images of the sample while an Energy Dispersive X-Ray Analyzer (EDX or EDA) is also used to provide elemental identification and quantitative compositional information.

As mentioned in the introduction, the patterning device (mask or reticle) is another critical component that is subject to handling operations, and reticle contamination or other defects can be another cause of poor performance in patterning. Reticles 246 are not usually handled as frequently as the substrates 230, 232, 234, but they are swapped in and out of the lithographic apparatus 200 whenever there is a change in the product pattern being applied to substrates (different product or different layer). A reticle inspection apparatus 248 is provided for inspecting the reticles directly for contamination and other defects. A reticle handling system is indicated schematically at 249. For a transmissive reticle such as that shown in FIG. 1, the clamping arrangement may contact side portions of the reticle at the front and/or back side. For a reflective reticle, as used in an EUV lithographic apparatus, then an electrostatic clamp will normally be used at the back side of the reticle. Again, contamination or other defects can be on the reticle, or can be on the reticle support MT, and can be transferred from one to the other during operation.

Each of the inspection apparatuses 240, 244 and 248 is shown as a unit separate from the lithographic apparatus and other processing apparatuses of the system. This is for the sake of example only, and any or all of these inspection apparatuses can be integrated into the lithographic apparatus, for example. Some known EUV lithographic apparatuses have reticle backside inspection integrated, so that reticles do not need to leave the vacuum environment for inspection.

The following description will concentrate on substrate backside contamination as a type of defect to be analyzed.

The same principles can be applied readily to the issue of reticle defects. Indeed, it may be a question for the system operator, whether an observed loss performance may be caused by substrate contamination or reticle contamination. Generally, it is possible to determine at a preliminary stage, whether defects are on the reticle (or associated support) or on the substrate (substrate support). This is because defects on the reticle will cause similar effects in repeating across all fields on a substrate, whereas a defect on a substrate will not.

In order to provide automated tools for analyzing the effect and root cause of backside contamination in lithographic production systems, there is now disclosed the provision of diagnostic apparatus 250, as illustrated at the top of FIG. 2. The diagnostic apparatus 250 is a data processing apparatus implemented by a combination of computer hardware and software, connected to receive data from the manufacturing system just described. The computer hardware can be located physically on the same site as the litho tool and other apparatus, or it can be located remotely and connected by telecommunications channels and/or removable storage. The diagnostic apparatus 250 operates by finding correlations between different types of measurement data relating to the same substrate, or at least relating to other substrates undergoing similar processing. Diagnostic information 252 is output by the apparatus.

In some embodiments, we refer to these different types of measurement data as "inline data" and "offline data". This reflects that the inline data can be based on measurements made during normal processing, for example alignment or height map data obtained from a substrate using the sensors AS, LS in the lithographic apparatus 200. (Similar data may be measured from a patterning device MA). The offline data, on the other hand, may be based on direct inspection of the substrate (or reticle) for defects, using inspection apparatus 244 or 248. Data from measurements by inspection apparatus 240 may be considered offline or inline data. Another way of regarding the different types of measurement data is that the first measurement data may relate to symptoms caused by defects such as backside contamination, while the second measurement data relates to observation of the defects that cause those symptoms. Behind that cause, there is somewhere in the whole lithographic manufacturing system a root cause of the contamination. The diagnostic information can be useful particularly for identifying that root cause more easily than in known systems.

Another way of distinguishing different types of data is to consider different types of measurement data as either intrinsic data or extrinsic data. Intrinsic data may be obtained by observation of the substrate (or reticle) itself, for example backside inspection. Extrinsic data may represent effects that only arise when the substrate (or reticle) is interacting with the substrate support (reticle support). Extrinsic data may be derived for example from height maps measured in the lithographic apparatus, or from overlay results obtained when patterns are applied in that apparatus. Such extrinsic data may be used as first measurement data, while intrinsic data is used as second measurement data.

In the system illustrated in FIG. 2, inline data 252 is supplied for example by lithographic apparatus 200 based on measurements made in the measurement station 202. Offline data 254 may be supplied by substrate backside inspection apparatus 244 and/or reticle inspection apparatus 248. Data 256 from inspection apparatus 240 may be considered inline data or offline data, depending on the mode of inspection. In the language of the introduction and claims, data 256 representing local deviations in a performance parameter such as overlay or CD would be used as first measurement data (inline data). Were apparatus 240 to be used directly for defect detection, data 256 might be used as the second measurement data (offline data).

The diagnostic information 260 may take many forms. In one example, a diagnostic map may be generated based upon defects and local deviations of the substrate, enabling particle contamination affecting focus and/or causing clamp performance issues to be pinpointed quickly without the need for system downtime. The diagnostic information may be further processed to identify particular handling operations or handling apparatuses as the root cause of contamination or other defects. This may be performed in combination with so-called context data CDAT. Useful context data may for example describe the processing history of a particular substrate, and even which particular apparatuses have been used in performance of those steps. Further, the diagnostic apparatus 250 may use a library 258 of "fingerprint" data, as described further below.

In some embodiments, the diagnostic information is used automatically or manually to update a maintenance schedule 262 for the production system. In some embodiments, the diagnostic information, for example the maintenance schedule, is applied directly and automatically in a supervisory control system 264 of the system. Supervisory control system 264 can for example automate interruption of processing by one or all apparatuses, either on a planned basis or on an emergency basis where further operation would simply spoil the processed substrates. Control commands 266 are issued to the various apparatuses of the system to implement the desired maintenance. Control commands 266 may include alarms to alert the operators. Control commands 266 may require human intervention or confirmation before being implemented.

Figure 3:
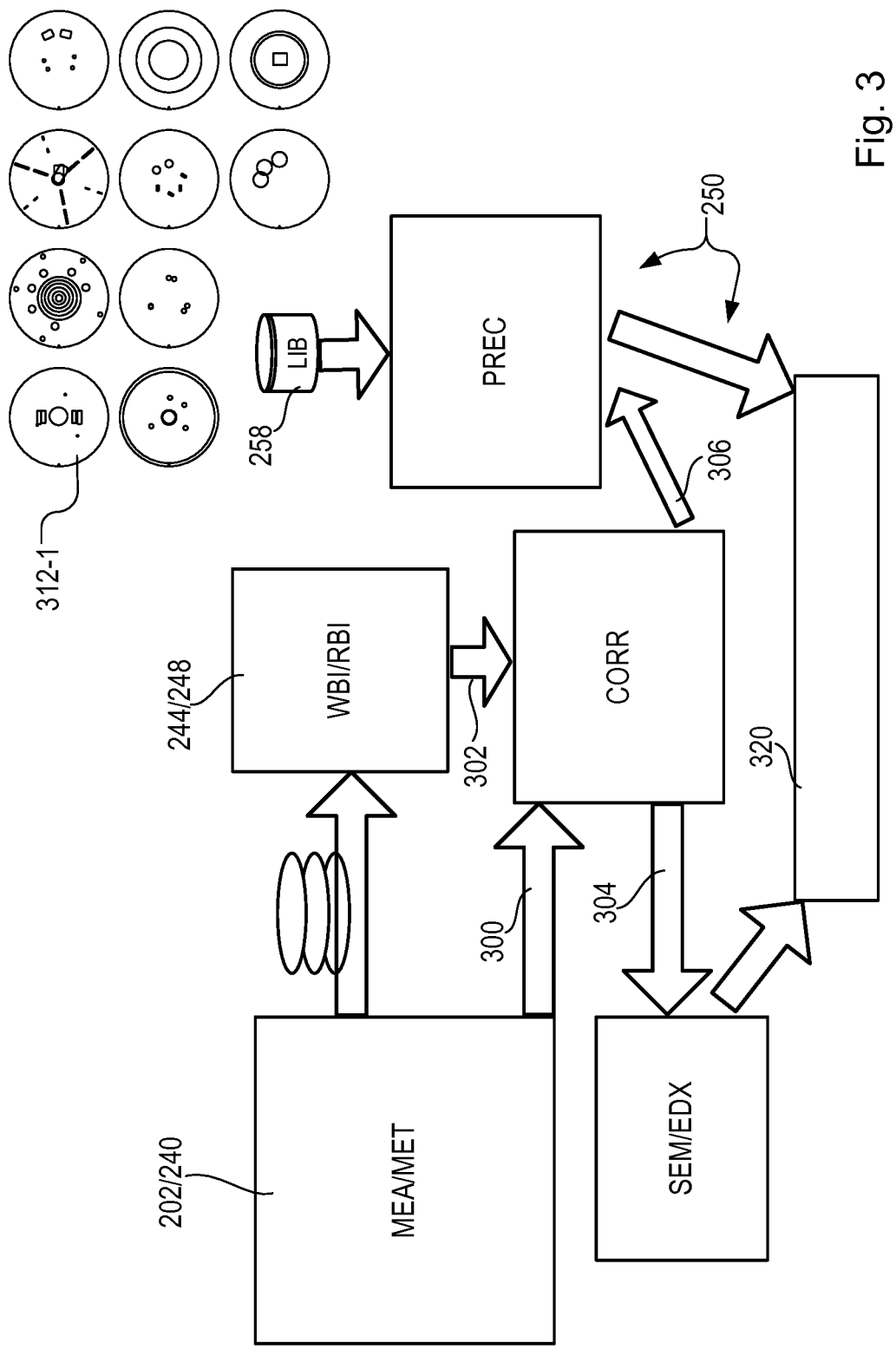
FIG. 3 schematically depicts workflow for utilizing the diagnostic apparatus in accordance with an embodiment of the present invention.

FIG. 3 schematically depicts workflow for utilizing the diagnostic apparatus in accordance with an embodiment of the present invention. The diagnostic apparatus 250 is used for monitoring and analysis of a lithographic 3o process performed on successive substrates, the lithographic process comprising a sequence of processing steps performed on each substrate, the processing steps including at least one patterning step performed in a patterning apparatus, one or more pre-patterning process steps and one or more post-patterning process steps, and each of the processing steps involving one or more handling operations. The diagnostic apparatus comprises a data processing apparatus programmed to perform automatically several steps. First measurement data is obtained, representing local deviations of a characteristic of the one or more substrates subjected to the lithographic process. The characteristic of the substrates may be for example a physical quantity such as surface height, surface roughness, texture, temperature, surface or bulk electrical quantities, such as electric field, current, voltage, charge, magnetic field effects, light emission, luminosity, stress or strain (birefringence).

The characteristic represented in the first measurement data may be a derivative of one or more measured properties, and need not be the directly measured property. For example, a characteristic might be local curvature (unflatness) of the substrate surface, which may be measured directly in some way, or can be obtained from height measurements as a second derivative. The characteristic of the substrates may alternatively be a performance parameter of the lithographic process, such as overlay or CD. In a practical embodiment, the processor of the diagnostic apparatus may receive raw measurement data from which it calculates whatever form of distribution of local deviations is desired. The first measurement data used in correlation with their second measurement data may be a processed form of measurement data, and may even combine the results of several individual measurements. Examples of this will be illustrated further below. In any event the term 'measurement data' is intended neither to be restricted to raw measurements, nor to exclude raw measurements.

Local deviations can be measured using any suitable measuring technique. Inline measurements can be ones made during the normal processing of the substrate, but the first measurement data may include any aspect of the local deviations that are measurable. This may be from a patterning apparatus, with the first measurement data being obtained from sensors within the patterning apparatus (lithographic apparatus LA 200). As already mentioned, level sensors LS and/or alignment AS are generally operated to measure positional deviations across the substrate in preparation for the patterning step. The same positional deviations can be used as the basis of the first measurement data. Alternatively or in addition, the same sensors can be operated before or after patterning, to obtain measurement data specifically for use in the diagnostic apparatus 250.

Additionally, before or after patterning, selected substrates may be sent for so-called offline measurement. These measurements form the basis of second measurement data 302, which represents a distribution of defects observed on one or more substrates subjected to the same lithographic process. This may comprise measurements from an inspection apparatus external to the patterning apparatus. For example, a backside defect map obtained by an inspection apparatus 244 may be used. Again, the second measurement data may be raw measurement data, or it may be processed and/or combined with other data. In particular, one or both of the first and second measurement data may be transformed in some way to make them more directly comparable with one another. Examples of this will be described below.

With the two sets of measurement data, the diagnostic apparatus 250 identifies a correlation between the distribution of defects represented in the second measurement data and a distribution of local deviations represented in the first measurement data. Diagnostic information relating to the lithographic process may then be generated based on the identified correlation. In other words, the first measurement data and second measurement data are used to identify one or more spatial correlations between defects represented in the second measurement data and local deviations represented in the first measurement data. Examples of performing the correlation are provided below.

The diagnostic information can take many forms, and be used in many different ways. In the illustrated example, the identified correlation is used to identify specific regions of the substrate (or patterning device) for further investigation. Based on correlation results 306, portions of the second measurement data related to the identified regions is retrieved and used to obtain diagnostic information relating to the patterning apparatus and/or other apparatus employed in the lithographic manufacturing process. Ideally the processor is further arranged automatically to update a maintenance schedule relating to at least one of the apparatuses employed in the lithographic manufacturing process.

The first measurement data 300 is received from the inline measuring apparatus which may be included within the patterning apparatus. The inline measuring apparatus may be for example the level sensor LS (height sensor) of the apparatus shown in FIG. 1. In another example the first measurement data is based on measurements made using level meter or an electrostatic voltmeter (ESVM) on a substrate table. When a level sensor is used this in effect produces height map data measured from a front side of the substrate.

As mentioned above, the substrates generating this first measurement data are also sent for offline inspection, for example using inspection apparatus 244. These offline measurements form the basis of second measurement data 302, which may be a substrate backside defect map.

The first measurement data has a first spatial resolution. The second measurement data has a second spatial resolution. Due to the very different nature of the inspection apparatuses or sensors used to obtain this data, their spatial resolutions may be very different. In the illustrated example, the second spatial resolution is higher than the first spatial density resolution. That is to say, the sampling density of measurements across the substrate is higher in the offline data (for example a detailed backside inspection result) than in the inline data (for example a height map). Accordingly, some pre-processing is required, before these two sets of data can be compared to identify correlations. Pre-processing may also be desired in order to select or at least accentuate a particular class of symptom, or a particular class of defect. To illustrate these options in a practical example, the first measurement data 300 and the second measurement data 302 can be compared as follows.

The higher-resolution second measurement data, which comprises measurement points at fixed or random positions, for example a regular pixel grid. This data is integrated over a grid defined by the (lower-resolution) first measurement data. In the case of height map data, for example, the lateral (X, Y) resolution is determined by the scanning path and sampling density of the level sensor LS. Z data contains post-processed sensor output. From the more detailed image of defects mapped using inspection apparatus 244, samples are summed up or averaged over the coarser grid of the height map data (first measurement data). In this way, the two sets of data are mapped to a common spatial sample pattern (pixel grid), and spatial correlation can be identified between them. In an example, second 3o measurement data is mapped to the grid of the first measurement data. In principle, both sets of data could be mapped to a different, common grid. For example this may be of interest where different sets of inline measurement data are to be considered in parallel.

As mentioned, the pre-processing of the first and/or second measurement data can also include selectivity of different features. The mapping can be repeated for different defect sizes intervals to distinguish smaller and larger defects. The data can be further converted using a weighting function (discussed in more detail below) to identify characteristics over a certain threshold. The first and second measurement data can be converted to a common scale, to help comparison. Then the first measurement data and second measurement data matrices are cross-correlated by multiplying them element-by-element. Optionally, this multiplication can be repeated after applying an increasing offset between the matrices in the x- and y-directions respectively. This produces data that is more sensitive to the smearing out of particle and particle cluster effects. Repeating with and/or introducing offsets may also be useful if accurate correspondence of positions within the two data sets cannot be taken for granted. Systematic offsets may also be known in advance or retrieved from correlation of the received measurement data. These offsets can be subtracted for subsequent measurements, as a form of calibration, instead of repeating with many different offsets each time.

The resulting correlation map can be used in different ways. At 304, for example, regions where correlation is identified are used to select portions of the substrate for further inspection and analysis using inspection apparatus such as SEM-EDX. At 306, on the other hand, the correlation map 304 can also be used to retrieve the most relevant portions of the high-resolution defect map that is in the second measurement data. This can be used to relate those defects that cause symptoms such as defocus and/or clamp performance problems to specific parts of the internal and external substrate handling system. One way of doing that is to use the library 258 which contains fingerprints 312-1 to 312-10 of different handling apparatuses. Each fingerprint is defined by those points at which a handling apparatus will make physical contact to support and/or grip the substrate (or reticle). Such fingerprint data can for instance be obtained empirically from backside inspection of specific monitoring wafers that have been cycled over the handling system of the processing apparatus in question. Alternatively or in addition, fingerprint data can be obtained from prior knowledge such as the design of the apparatus.

In an example method, these fingerprints are used for pattern recognition PREC within the diagnostic apparatus 250 described below. Optionally combining the results of SEM-EDX and pattern recognition at 320, the apparatus can obtain quite specific indications as to the root cause of those defects that are affecting overall system performance.

Figure 4:
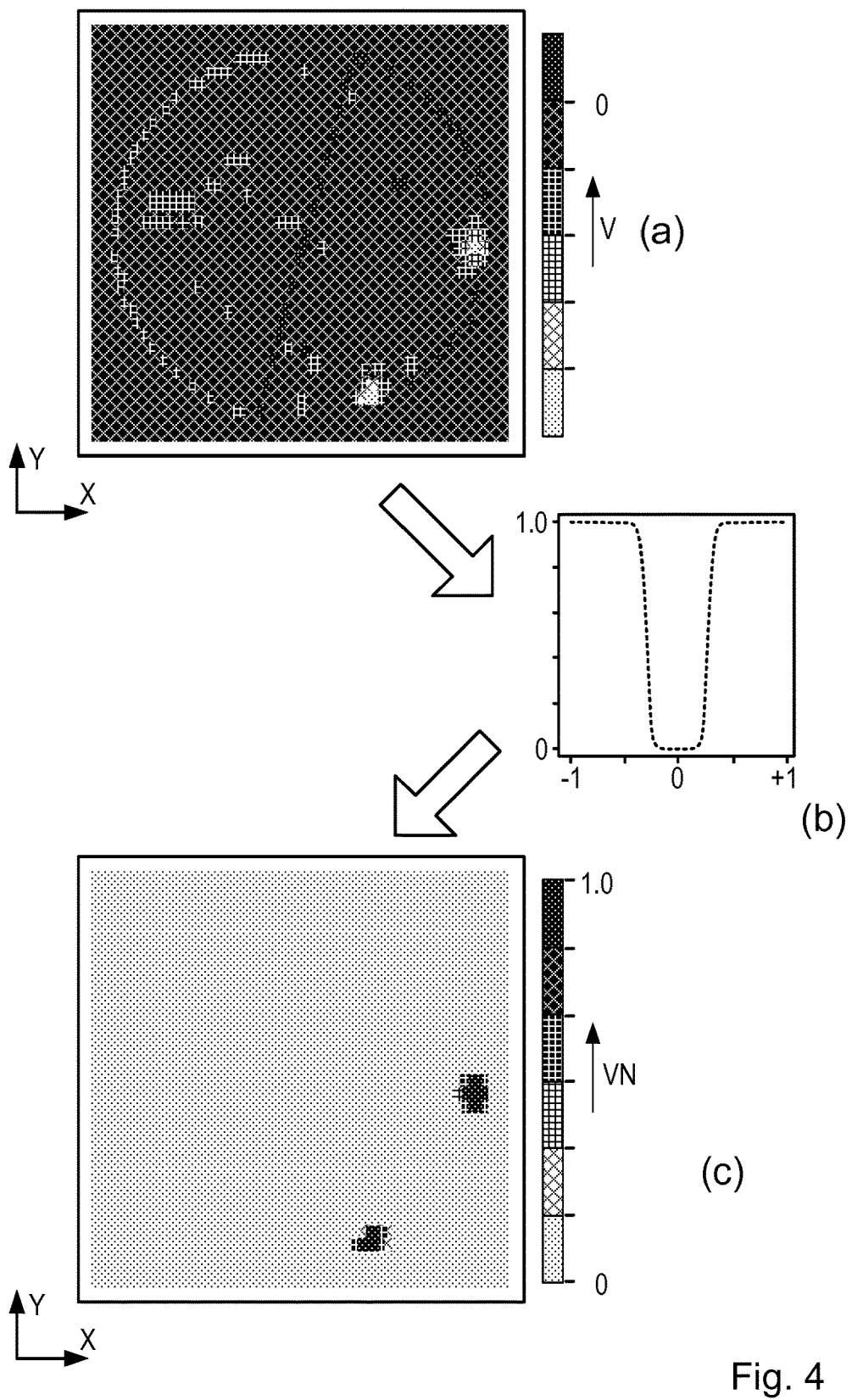
FIG. 4 (*a*) shows a plot of first measurement data in accordance with an embodiment of the present invention.
Figure 4:
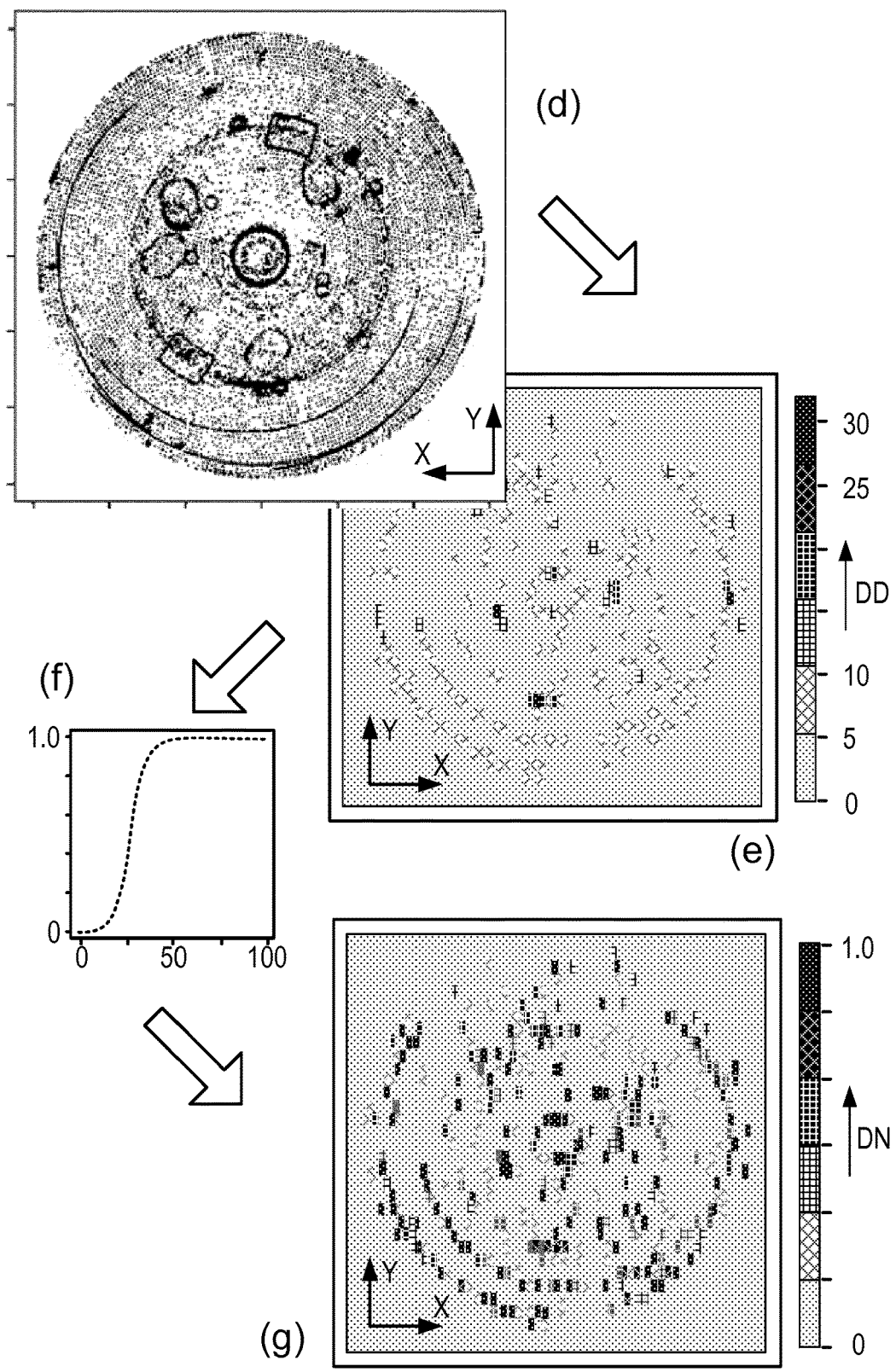

FIG. 4 illustrates schematically the method of creating cross-correlated data using the apparatus in accordance with the present disclosure. Firstly the first measurement data will be discussed. FIG. 4 (a) shows a plot of first measurement data. It will be appreciated that in practice a fine gradation of values can be represented. The plot has been rendered into a crude scale with black and white hatching purely for compliance with patent formalities. In this example the data comprises ESVM (electrostatic voltmeter) data on an X-Y grid. Highlighted regions (cells) represent local increases in voltage V. In another embodiment, these could be height (or curvature) values. Such measurements can be performed after a substrate is unloaded from the substrate support, and will reveal regions where contamination may be causing non-uniformity in the electrostatic clamping force. At FIG. 4 (b) we show a weighting function based on (for example) a Gaussian curve. This is for normalizing the ESVM data of FIG. 4 (a). The weighting function in this example is symmetric and bipolar because the ESVM voltage can be bipolar. At FIG. 4 (c) we plot dimensionless weighted data VN, based on the combination of the ESVM data when subjected to the asymmetric weighting function. In this example, the only regions highlighted in the plot of FIG. 4 (c) are those with a voltage above the threshold dictated by the weighting function. This in effect is the generation of a deviation map where a density value per region is subjected to a dimensionless weighting function to accentuate the values above a certain threshold prior to the correlation step. Values of the data pre-processed in this way lie on a scale of (for example) 0 to 1.

FIG. 4 (d) (second page) shows an example of the second measurement data, in this case a map of substrate backside defect data on a plot of position relevant to an x-y axis plot. The second measurement data includes defect maps measured by an inspection apparatus 244 or the like directly inspecting a reverse side of the substrate. The data of FIG. 4 (d) is very detailed in spatial resolution. It also shows defects that are trivial and will not be the cause of performance issues. In practice, the data of FIG. 4 (d) also contains a lot of greyscale information, although it has been rendered in binary form for the purpose of this patent illustration. A number of fragments of different ones of the fingerprints 312-1 etc. are overlaid in the data. Also present are numerous burl dots and one or two larger defects such as scratches.

At FIG. 4 (e) we see a plot of defect density DD that is the number of observed defects summed up in each cell of a coarse grid that is designed to be the same as the grid of the ESVM measurements in FIG. 4 (a). Again, filtering or selection can be applied to highlight particular defect sizes. FIG. 4 (e) for example shows a summed plot of defect density for a 1-5 μm defect size range, based on offline measured data. Again, in order to facilitate comparison a dimensionless weighting over a threshold based on a cumulative Gaussian curve is applied, as illustrated at FIG. 4 (f). Values DN lie on a scale of (for example) 0 to 1. This results in the defect density plot of FIG. 4 (g), which illustrates the weighted defect density in the range 1-5 μm based on the second measurement data and the weighting function. This process may be repeated as desired for other ranges of defect size. Parameters of the weighting function can be varied.

Figure 5:
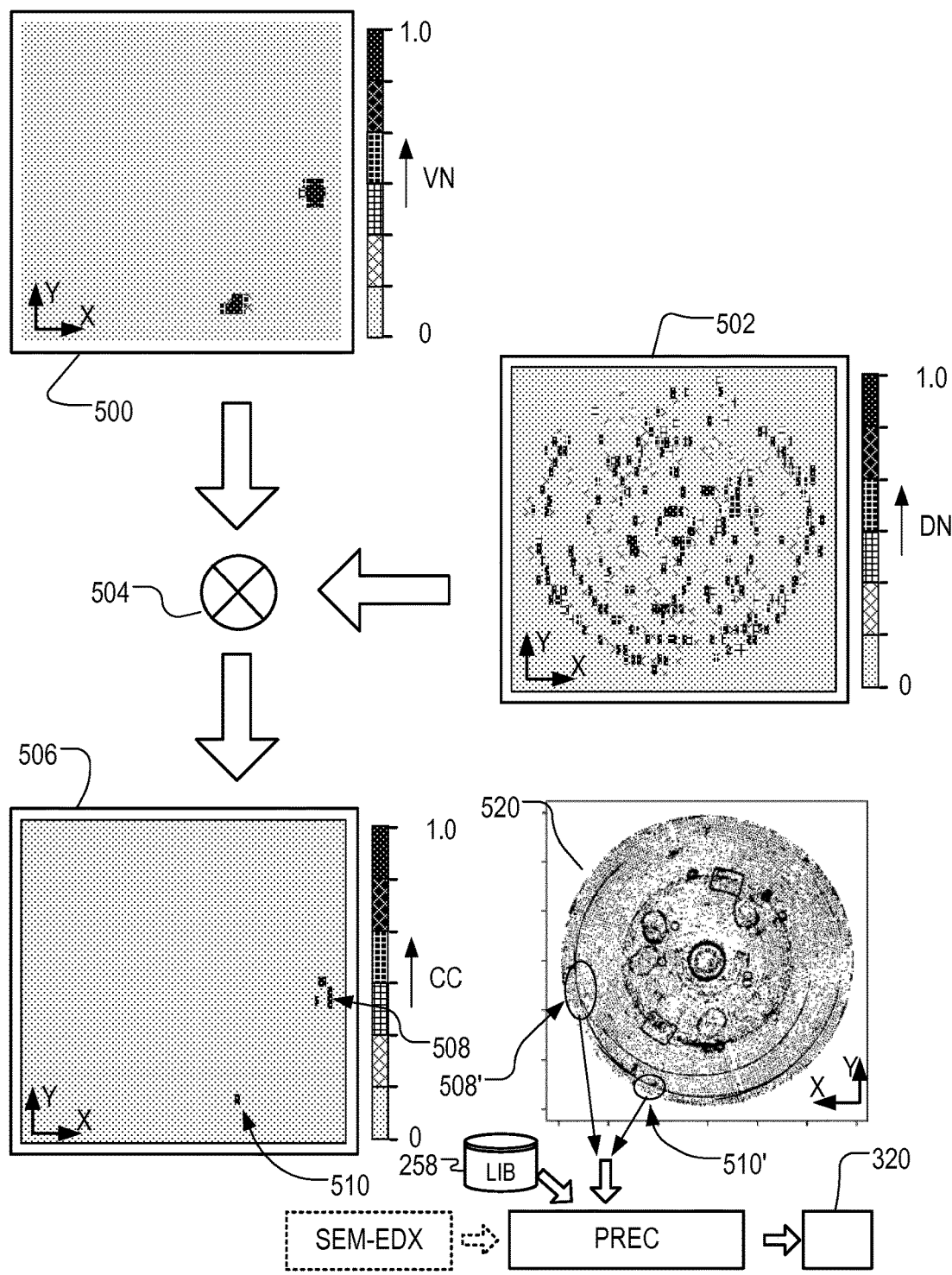
FIG. 5 illustrates the step of identifying correlations between first measurement data and the second data measurement and optionally generating additional diagnostic information in one embodiment of the diagnostic apparatus.

FIG. 5 illustrates the cross-correlation operation comparing the first measurement data 500 with the second measurement data 502. First measurement data 500 is shown as at FIG. 4(c), that is after pre-processing and conversion to the dimensionless scale. Similarly, the second measurement data 502 is shown in its processed state, on the same spatial grid as the first measurement data 500 and on the same dimensionless scale. At 504 these two matrices or arrays of values are multiplied element by element to obtain a correlation map 506.

The cross-correlation step 504 can be repeated as desired by applying X and Y direction offsets to create further maps.

Whereas the defect map at 502 is very "busy" with many defects to consider, it will be seen that the correlation map 506 shows only a few very specific portions (groups of cells) where correlation has been identified between the inline and offline data. These portions are highlighted at 508 and 510. Immediately the search for causes of degraded performance is greatly simplified by the production of diagnostic information such as a correlation map 506. Particular benefit is obtained when the correlation map is used in combination with the original higher-resolution measurements.

Further, at 520 we see selection of regions of interest within the high-resolution second measurement data, based upon the identified correlation. This illustrates the front side of the substrate with the regions 508', 510' highlighted, where correlation was found at 508 and 510 in the (low resolution) correlation map. Compared with the low spatial resolution of the first measurement data and the correlation map itself, the high resolution data from these regions allows a much better recognition of finger print patterns. Furthermore, often, only a (not necessarily specific) fraction of defects of one fingerprint contributes to local deviations of the substrate during operation. For example, considering the typical case where material from substrate-contacting portions of a handling apparatus becomes adheres to the back side of processed substrates, it is extremely unlikely that material from all portions will suddenly transfer to one substrate on one day. A more likely scenario is that material from different portions of the apparatus gradually transfers to different substrates over a period of time. Therefore, taking only the local deviations into account, their origins will be difficult to identify. Putting the relevant defects in the "fingerprint" context as disclosed herein allows the affected handling apparatus to be identified making maximum use of available data. As mentioned, it may also be desirable to generate instructions to make measurements of material composition at locations indicated by the second measurement data and the identified correlation as part of the generation of diagnostic information. This may be used in addition to the pattern recognition function PREC to identify potential causes of defects. For example, where pattern recognition indicates two different handling operations as potential causes of contamination, the material composition may help to determine which of those apparatuses is the true source.

As mentioned, contamination of the reticle may be a cause of degraded performance, as well as contamination of the substrate. The same method can be repeated with second measurement data from reticle inspection apparatus 248 to identify correlation between symptoms observed in the first measurement data and defects observed on the reticle. It is a matter of choice whether both types of inspection and cross-correlation are done as part of every analysis, or whether reticle inspection and substrate inspection are done separately. As an option, for example, reticle inspection could be ordered (by human intervention or automatically by the diagnostic apparatus), when substrate inspection has not revealed a likely cause. As noted above, reticle inspection will be particularly advisable when local deviations in the first measurement data repeat with the same frequency and spatial distribution as the fields being exposed on the substrate. Similarly, substrate inspection could be ordered when correlation with reticle inspection has not identified a likely cause. It may convenient to regard the reticle defect map effectively as third measurement data. In the language of the introduction and claims, either the substrate defect map or the reticle defect map can be regarded as the second measurement data.

In the case where reticle defects are suspected and a reticle defect map is used as the second measurement data, the first measurement data used to identify a correlation may represent an intrafield component of the local deviations over the substrate as a whole. This intrafield component may be obtained for example by averaging the local positional deviations across every field (target portion) of the substrate.

As mentioned, the first measurement data may include measurements of one or more performance parameters of the patterns applied to the substrate. These performance parameters may be measured on a front side of the substrate by an optical inspection/metrology apparatus 240. This may be an overlay error, being a positional deviation between features applied in two or more distinct patterning steps (see below). The same processing can be applied as described above. In a practical implementation, different types of first measurement data may be processed in parallel, and results combined to improve the quality of diagnostic information.

Figure 6:
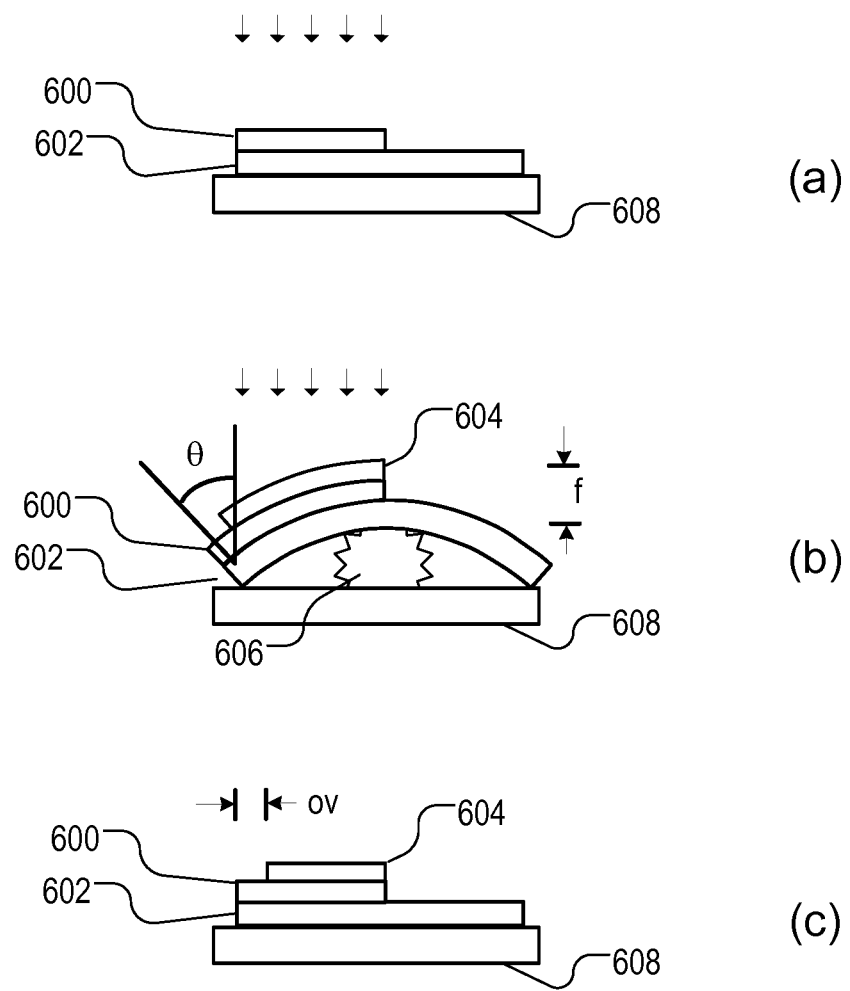
FIGS. 6 (*a*), 6 (*b*) and 6 (*c*) depict schematically the generation of focus and overlay errors on the front side of a substrate due to the presence of contamination.

FIG. 6 depicts schematically the generation of focus and overlay errors in a patterning step, due to the presence of particle contamination on the substrate backside (or on the substrate support). In the example lithographic process, a first pattern is to be applied to form product features in a first layer 600 on a substrate 602. A second pattern is then to be applied to form product features in a second layer 604 overlying the first layer.

FIG. 6 (*a*) shows the ideal situation of perfect flatness of the substrate. The lateral positions and height (focus) of the first layer 600 and the substrate 602 are well defined. FIG. 6 (*b*) shows the effect of a contaminant particle 606 located between the substrate and its support 608 (WTa or WTb, for example in FIG. 1) during patterning of the second layer 604. The substrate bulges locally over the particle instead of lying flat. When the second layer 604 is patterned 60 due to the local curvature of the substrate 600 over a particle 606 between the backside of the substrate 602 and the clamp (not shown), a focus error f is generated, which will degrade patterning performance and affect CD for example. Further, positions of features in the first 602 and second 604 layers 60 on the sloping sides of the bulge are not in registration. The edge of the substrate 600 and the first layer 602 lie at an angle θ to the vertical due to the local curvature of the substrate 600.

Once the second layer 604 has been exposed and the substrate 600 removed from the clamp it is clear that there is now an overlay error OV present, as shown in FIG. 6(*c*). This illustrates that rather than being in proper registration, the feature of the second layer 604 lies inward of the edges of the first layer 602 and the substrate 600.

Figure 7:
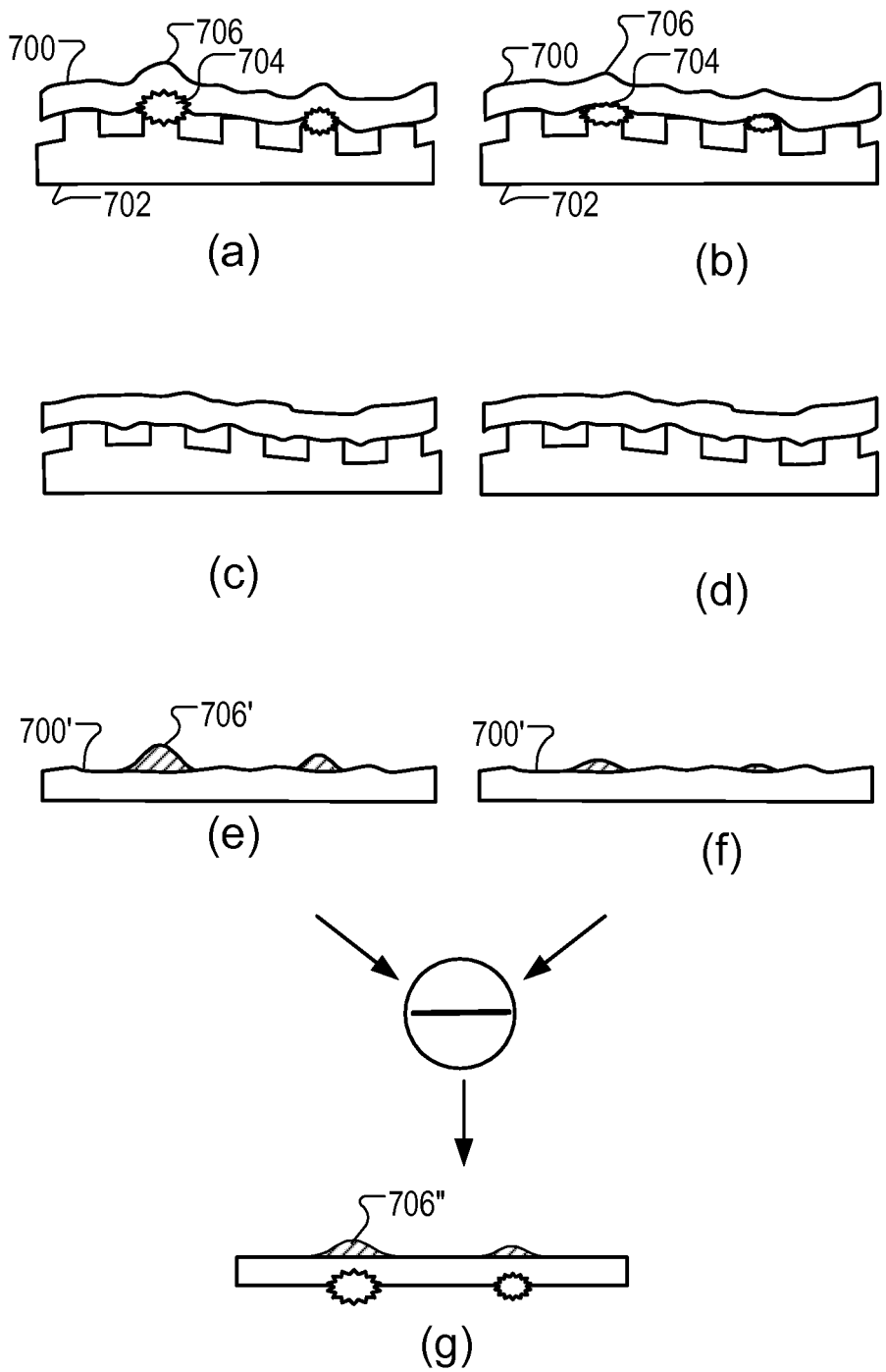
FIGS. 7 (*a*), 7 (*b*), 7 (*c*), 7 (*d*), 7 (*e*), 7 (*f*) and 7 (*g*) illustrate a method of obtaining filtered height map data, useful for example as improved first measurement data in the diagnostic apparatus of FIGS. 2 to 5

Referring now to FIG. 7, there is now disclosed a method of obtaining height map data in a form which discriminates between local height variations which are the effect of backside contamination and deviations caused by other effects. When measuring a substrate height map, such as that forming first measurement data generated inline using a level sensor, the resulting height profile is the sum of several contributions: local effects due to the presence of particles on the backside of the substrate; global effects due to the substrate clamp having a non-flat surface; global and local effects due to the roughness and non-flat surface of the substrate; local effects due to sagging of the substrate in the regions unsupported by the clamp; local effects in the region of the edge of the substrate and global effects due to thermal gradients, to name but a few. Ideally for a diagnosis of performance issues caused by contamination, measurements should show only those substrate deformities that are due to the presence of particles on the backside of the substrate. This data may be useful in itself, but also can serve as good quality first measurement data in the diagnostic apparatus described above.

The inventors have recognized that it is possible to remove systematic and global effects by using pre-defined sets of reference data. This can be done by using corresponding filtered height maps obtained under different clamping conditions. For example, the different clamping conditions may be different clamping pressures. In an electrostatic clamp, different clamping conditions could be obtained by using the same magnitude of clamping voltage, but with opposite polarities.

FIG. 7 (*a*) shows schematically a map of measured surface height of a substrate at a low clamping pressure. A substrate 700 is held on a clamp (substrate support) 702, and contaminant particles 704 are held between the substrate 700 and the clamp 702 in contact with the backside of the substrate. The presence of the particles 704 causes distortion 706 on the front side of the substrate 700. This is recorded in height map data measured from a front face of the substrate. This data may be measured by a patterning apparatus while the substrate is loaded into the patterning apparatus for a patterning step of a lithographic process, or may be measured after the substrate is removed from the substrate support after the patterning step. Then, without removing the substrate 700 from the clamp 702, the clamping conditions are changed. In an example method, the pressure is increased. A map of measured surface height of the substrate at a high clamping pressure is obtained, including deviations 706, as illustrated schematically in FIG. 7 (*b*). At higher clamping pressures the effects of particles 704 on the substrate 700 are less than at low pressures since (in this particular example) the increased pressure compresses the particles 704 somewhat. The first height map data and the second height map data are therefore measured with the substrate 700 being subject to different clamping forces whilst on the same clamp 702. Alternatively, the substrate 700 may be subjected to different polarities of clamping charge on an electrostatic support to measure the first height map data and the second height map data.

The next step is to remove all global features in each map. This is done by subtracting pre-defined reference height maps from the maps measured at FIG. 7 (*a*) and FIG. 7 (*b*). The reference maps are regarded as being free of defects, and are created by measuring the height maps of very clean substrates on a very clean substrate support (clamp), for example, after installation and qualification of a new system. Reference maps are measured at exactly the same clamping conditions as the height maps shown at FIG. 7 (*a*) and FIG. 7 (*b*), respectively. creating the reference maps shown at FIG. 7 (*c*) and FIG. 7 (*d*). Alternatively, if such reference maps are not available, they can be created by combining data from low- and high-pass filtered data of the deformed substrates in question. The subtraction of the reference maps effectively filters each of the measured height maps by removing global features due to the effects of the substrate clamp itself. This creates a difference or "delta" height map at low pressure, as shown schematically in FIG. 7 (*e*), and a delta height map at high pressure, as shown schematically in FIG. 7 (*f*). As illustrated by the flat underside of substrate 700' in the delta height maps, the height variations of the clamp 702 have been canceled out by the subtraction of the reference height maps.

Each of these delta maps still contains features and effects due to local variations in substrate height. Features due to edge effects and substrate sag are also present in the reference height maps as well as the low pressure and high pressure height maps, and so are removed at the delta map stage. These delta maps are filtered yet further to remove local substrate height features by subtracting the data of the high pressure delta height map from the low pressure delta height map, which leaves only the delta particle, map, in other words, the particle contamination. This is illustrated schematically in FIG. 7 (*g*), which shows schematically the delta particle map created using the delta height maps depicted in FIGS. 7 (*e*) and 7 (*f*).

The signal-to-noise ratio of the delta maps is determined mainly by noise during measurement, and hence it is possible to reveal features 706' with heights of the order of nanometers in the delta particle map. Clamping pressure in known apparatuses can be expressed in millibar (mbar). In known handling apparatuses for semiconductor wafers, clamping pressures on the order of 100 or several hundred mbar are customary. Furthermore, clamping pressure can be made adjustable over quite a wide range, for example so that the "high" pressure applied during measurements of FIG. 7 (*b*) and FIG. 7 (*d*) may be two, three or four times greater than the "low" pressure applied during measurements of FIG. 7 (*a*) and FIG. 7 (*c*).

Even micron-sized particles will result in an elastic deformation of the substrate of the order of a few nanometers, and varying the clamping pressure can result in a factor of two size difference. Actual particle co-ordinates can then be determined easily based on the delta particle map alone. In addition to X-Y coordinates, each particle can be characterized by one or more parameters such as height, radius/diameter. This facilitates targeted inspection and possibly cleaning of the appropriate portions of the substrate/reticle backside, and the substrate/reticle support.

Further, if the delta particle map is used as first measurement data (instead of raw height map or curvature data or as a supplement to those) in the diagnostic apparatus disclosed above, the first measurement data is based upon a highly accurate inline measurement process.

Returning to the diagnostic apparatus 250 itself, it will be seen that a processor may be arranged to use first measurement data and second measurement data to identify correlation between observed defects local deviations in some characteristic of the substrate. A deviation map representing a distribution of local deviations in multiple regions distributed spatially some characteristic or performance parameter across the substrate may be generated using the first measurement data. A defect map may be generated representing a density of defects observed in regions corresponding in spatial distribution with the regions of the deviation map may be generated using the second measurement data. The first measurement data and second measurement data may be for example inline data and offline data, as defined above. The first and second measurement data may be extrinsic data and intrinsic data, as defined above.

In any case, regions where the density of defects in the defect map is correlated with the density of local deviations in the deviation map may then be identified by the diagnostic apparatus. Generating diagnostic information after the correlation has been identified may include retrieving high resolution defect data related to the regions where correlation is identified from the second measurement data and using this to generate the diagnostic information. Varying offsets in the definition of corresponding regions between the deviation map and the defect map may be allowed as part of the correlation process.

We now discuss the application of the diagnostic apparatus in the context of the "life cycle" of a substrate as it is processed from a virgin substrate to a finalized product. Each process the substrate undergoes (oxidation, cleaning, metrology, classification, measurement of focus and overlay defects, even the track along which the substrate travels) leaves a fingerprint of contamination that is unique and can be stored in a pre-classified database (for example library 258). This enables the identification of individual sources of contamination using a pattern recognition algorithm. When used in conjunction with the correlation map above enables the root cause of any contamination to be found. Importantly, the techniques disclosed herein enable such analysis to be substantially automated and performed more quickly than possible using human experts.

The diagnostic apparatus disclosed above can apply pattern recognition to the defect map using information about which defects which are identified as correlated with the first measurement data. It will be appreciated that the substrate backside inspection will show a vast number of defects matching the various chucks, clamps and pins used by the various apparatuses that the substrate passes through during its production lifecycle. Referring again to the highlighted portions 508', 510' in the high-resolution defect map in FIG. 5, pattern recognition can be applied specifically to identify the causes of those particular defects, based for example upon distance and a histogram of frequency of distance.

The generated diagnostic information may identify a specific handling step in the lithographic process. Using the pattern recognition and fingerprint approach allows the identified correlation to identify specific defects within the second measurement data, and using characteristics of the specific defects to identify a specific handling step in the lithographic process. Where this is done, an updated maintenance schedule relating at least in part to cleaning of a substrate support or reticle support within the patterning apparatus can be generated. Alternatively or additionally, the updated maintenance schedule 262 relates in part to a handling apparatus involved in a handling operation that is part of the lithographic manufacturing process.

The step of generating diagnostic information may include recognizing from the identified correlation which, if any, of the defect fingerprints matches a spatial distribution of defects in the second measurement data, with specific reference to features correlated with the distribution of local deviations represented in the first measurement data. The processor may be arranged further to use context data identifying individual processing apparatuses used for a given processing step on the substrate, if the lithographic processing involves the use of more than one processing step. In addition, the processor may be further arranged to generate advice to target and eliminate an identified cause of defects from the diagnostic information.

For example, the database may contain ten different fingerprint templates or images 320-1, to 320-10, one for each of the handling operations of FIG. 2. Each defect fingerprint represents a spatial distribution of defects associated with a specific handling operation in the lithographic process. When viewing a defect inspection image of a substrate, a pattern recognition algorithm can be used to recognize which specific fingerprints are present (or are potentially present) on the backside of the substrate. The algorithm in one example uses a combination of Delaunay triangulation with the generation of a Hausdorff distance to determine which of the ten templates match the observed defects. Numerous implementations of such a technique can be envisaged by the skilled person, based on the present teaching. One possible implementation will be described, purely by way of example.

Figure 8:
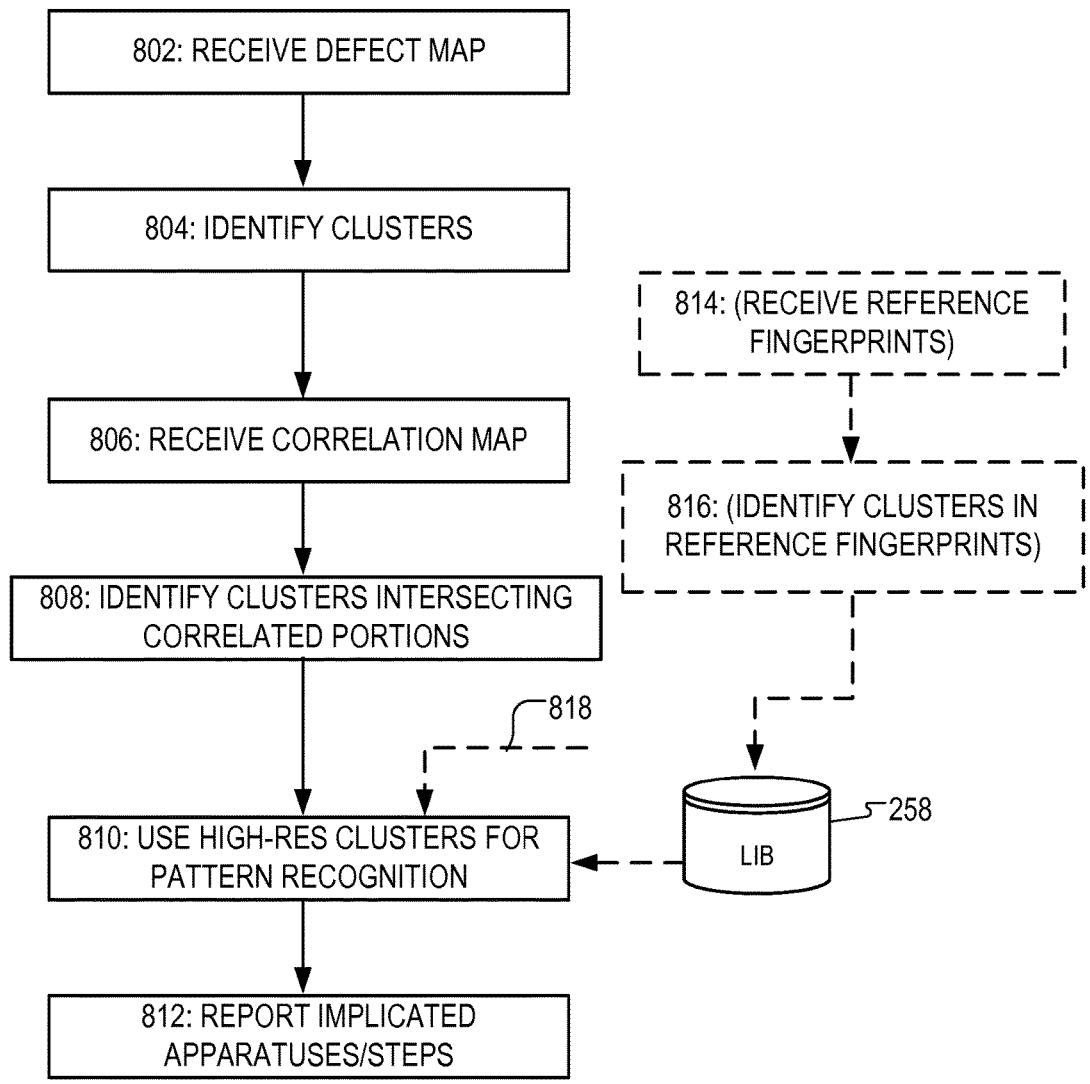
FIG. 8 is a flowchart of an example pattern matching process in the diagnostic apparatus according to one embodiment.

FIG. 8 is a flowchart showing key steps in the example process. At step 802, the defect map (second measurement data) is received. At 804 clusters of defects are identified within the defect image, to identify large-scale features within the data. For example, in the defect image of FIG. 4(*d*), large scale features such as ring-shaped marks of various shapes and sizes can be recognized among a lot of finer detail. Identifying clusters of points allows these features to be recognized and classified. One known algorithm that may be used for this is Delaunay triangulation. In this technique, the data processing apparatus creates a triangulation of a series of points P where each triangle in the triangulation is circumscribed by a circumcircle, and each circumcircle is empty of points. In other words the minimum angle in each triangle of points is maximized. Other techniques may be used to identify clusters. It may be appreciated that, in general, the fingerprints of some handling apparatuses may be rotated randomly relative to the orientation of the wafer, while other handling apparatus always handle the wafer in a well-defined orientation. The algorithms can be implemented to take such rotation into account.

At 806 the correlation map 506 between the first and second measurement data is made/retrieved, which has been obtained as illustrated in FIG. 5. At 808 the correlation map is used to identify portions (508', 510') of the high resolution data corresponding to the regions where correlation has been observed. At 808 clusters of points in the defect map which intersect the identified portions are identified within the detailed form of the second measurement data (FIG. 4(*d*)). While the version of the defect map used to identify correlation is rather coarse in spatial resolution and thresholded as well, the original defect map still contains high resolution, finely graduated data. Within this high-resolution data, clusters identified at step 804 are defined also with high resolution. Those clusters which intersect the identified portions (508, 510') are retrieved so that the full high resolution data can be used for the next step of pattern recognition.

At 810 the high resolution cluster data is used for pattern recognition against the library of apparatus fingerprints. For this recognition task, a Hausdorff distance (or modified Hausdorff distance) can be used to identify the sources of defects from the database of pre-classified fingerprint or template images. Iterative processing can be used in the clustering step and/or in the recognition. Every spectral component identifies an individual density peak that can also be used in further refinement of the pattern recognition.

For more information on the techniques mentioned, see "Comparing Images Using the Hausdorff Distance" by Huttenlocher et al, IEEE Transactions on Pattern Analysis and Machine Intelligence, Vol 15 No 9 (September 1993); "A Modified Hausdorff Distance for Object Matching" by Dubuisson and Jain, Proc. International Conference on Pattern Recognition, Jerusalem, Israel, pp 566-568 (1994); and "Shape Matching and Object Recognition Using Shape Contexts" by Belongie et al, IEEE Transactions on Pattern Analysis and Machine Intelligence, Vol 24 No 24 (April 2002). So far as the inventors are aware, these techniques have not been applied before in recognizing features on semiconductor substrates.

At 812, diagnostic information is generated that includes an identification of those fingerprints, that is to say those apparatuses, or at least apparatus types, that are implicated as sources of significant defects, by virtue of the correlation.

Steps 814 and 816 illustrate, for the sake of example, some processing that can be applied to the reference fingerprints 312-1 etc, to prepare for the pattern matching in step 810. Steps 814 and 816 may be performed at a different time and place from the other steps of the method. As mentioned above, the library 258 might consist of high resolution data similar to 802, representing reference fingerprints of specific handling apparatuses and process tools. The data may be obtained empirically by cycling test substrates multiple times through the apparatuses in question. The data may be obtained alternatively or in addition from design data of the apparatuses. At 814, the reference fingerprint data is received. At 816, clustering is applied to the reference data to identify larger scale features, in the same was as clustering is applied (or will be applied) to the second measurement data in step 804. A reference fingerprint typically consists of one or more such larger scale features, and these can be identified by the clustering and recorded in the library 258 for use in the pattern matching.

In the pattern matching step 810, prior knowledge 818 may be used so that only relevant fingerprints might be selected that correspond to the history of the substrate. For example, a fingerprint can be excluded from consideration in pattern matching, if the substrate in question has never encountered a handling apparatus of that type in its processing history. Then, at 810 pattern matching is done between the selected candidate fingerprints and the high resolution clusters that contain the defects that correlate to the first measurement data (808). Alternatively, matching can be done against all fingerprints, with prior knowledge used to filter the results so that apparatuses not involved in the history of the substrate are not implicated in the report at step 812.

It should be understood that the sequence of steps in the flowchart of FIG. 8 is not the only possible sequence. In an alternative embodiment, step 810 can be performed prior to step 806. That is to say, pattern matching can be performed against a range of candidate fingerprints, without reference to the result of correlation. The correlation result can then be used to filter out fingerprints that appear to match the observed defects, but do not necessarily contribute to the deviations in the first measurement data that are of particular interest. The correlation result can be used both before and after pattern matching, if desired.

It should be understood that the specific pattern matching techniques mentioned above are presented only as suitable examples. Other pattern matching techniques and modifications of the above techniques can be applied, if preferred. The main point of the present disclosure is that the correlation map provides an additional key that can be used in conjunction with pattern matching, to identify automatically the results that are relevant to the deviations observed in the first measurement data. As described above, the correlation can be used as a filter to determine those parts of the data on which pattern matching (of whatever kind) should be applied. Alternatively or in addition, the correlation result can be used as a filter to select relevant results after pattern matching has been performed.

Even within the method illustrated in FIG. 8, there are many choices that can be made in the detailed implementation of the pattern recognition and the method as a whole. For example, it may be that pattern recognition in step 810 is performed in two stages. Firstly, recognition may be performed on the basis of individual clusters, comparing the observed clusters against a library of component features. Once features have been recognized from the clusters, a larger handling apparatus fingerprint may be recognized by reference to the set of recognized features and their spatial relationship. Alternatively, each apparatus fingerprint may be recognized directly as a whole, in the pattern matching step 810.

In another aspect, the present invention also provides a computer program product for example a non-transitory memory device, having stored thereon software that when run on a computer causes the computer to carry out the steps of: receiving first measurement data representing a distribution of local deviations of a characteristic of one or more substrates subjected to the lithographic process; receiving second measurement data, the second measurement data representing a distribution of defects observed on one or more substrates subjected to the same lithographic process; identifying a correlation between the distribution of defects represented in the second measurement data and the distribution of local deviations represented in the first measurement data; and generating diagnostic information relating to the lithographic process based on the identified correlation. A diagnostic report, maintenance schedule or other repair document may be generated using the diagnostic information. The instructions may include instructions for directly causing interventions in the lithographic manufacturing process.

The steps of the methods described above can be automated within any general purpose data processing hardware (computer). The apparatus may be integrated with existing processors, such as the processing unit shown in FIG. 2, the lithography apparatus control unit LACU shown in FIG. 1 or an overall process control system. The hardware can be remote from the processing apparatus, even being located in a different country.

Figure 9:
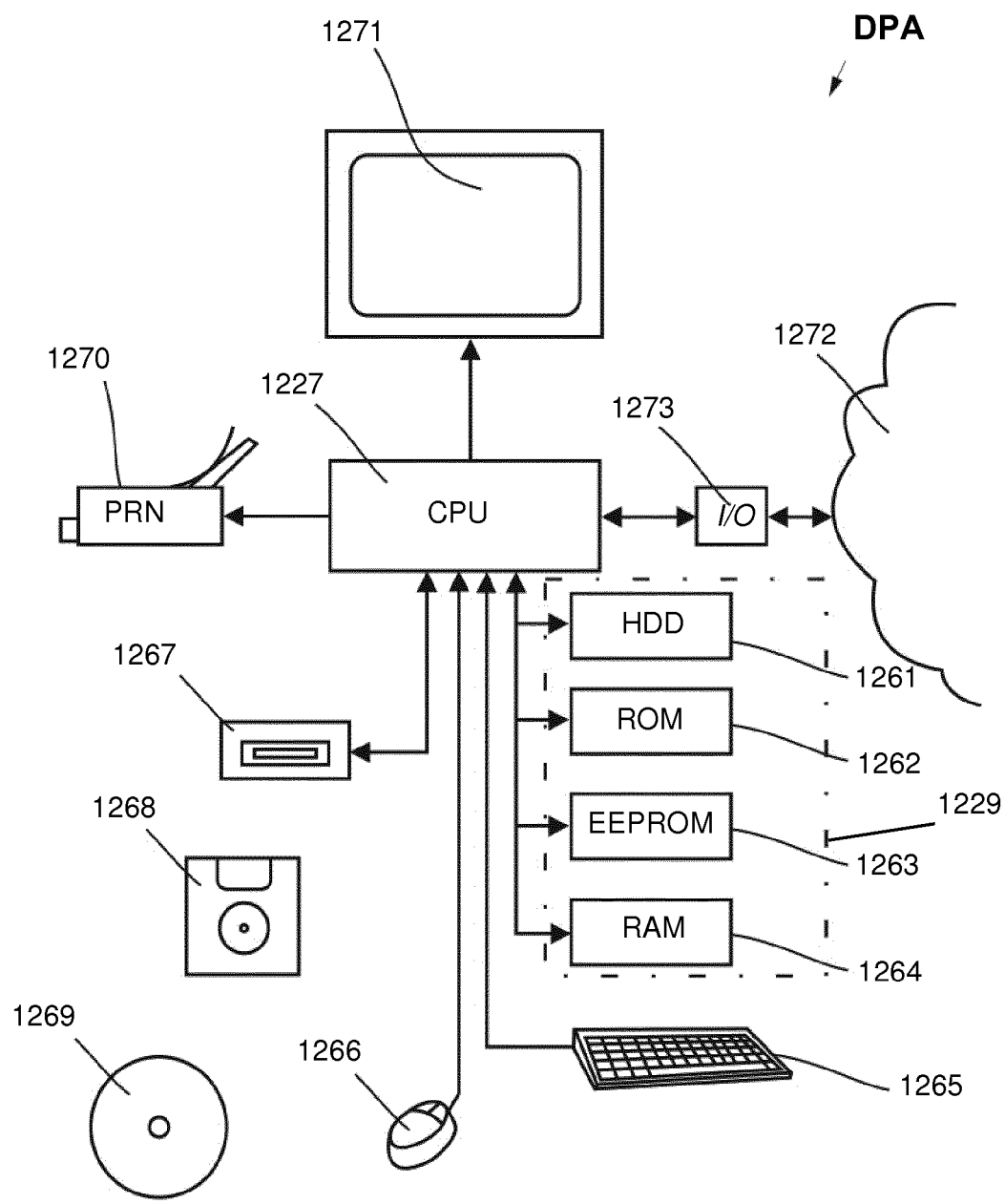
FIG. 9 illustrates schematically data processing hardware programmable to implement a diagnostic apparatus of the invention.

FIG. 9 shows components of a suitable data processing apparatus (DPA). The apparatus may be arranged for loading a computer program product comprising computer executable code. This may enable the computer assembly, when the computer program product is downloaded, to implement the functions of the inspection apparatus as described above.

Memory 1229 connected to processor 1227 may comprise a number of memory components like a hard disk 1261, Read Only Memory (ROM) 1262, Electrically Erasable Programmable Read Only Memory (EEPROM) 1263 en Random Access Memory (RAM) 1264. Not all aforementioned memory components need to be present. Furthermore, it is not essential that aforementioned memory components are physically in close proximity to the processor 1227 or to each other. They may be located at a distance away The processor 1227 may also be connected to some kind of user interface, for instance a keyboard 1265 or a mouse 1266. A touch screen, track ball, speech converter or other interfaces that are known to persons skilled in the art may also be used.

The processor 1227 may be connected to a reading unit 1267, which is arranged to read data, e.g. in the form of computer executable code, from and under some circumstances store data on a data carrier, like a magnetic disc 1268 or a CDROM 1269. Also DVD's or other data carriers known to persons skilled in the art may be used.

The processor 1227 may also be connected to a printer 1270 to print out output data on paper as well as to a display 1271, for instance a monitor or LCD (Liquid Crystal Display), of any other type of display known to a person skilled in the art.

The processor 1227 may be connected to a communications network 1272, for instance a public switched telephone network (PSTN), a local area network (LAN), a wide area network (WAN) etc. by means of transmitters/receivers 1273 responsible for input/output (I/O). The processor 1227 may be arranged to communicate with other communication systems via the communications network 1272. In an embodiment of the invention external computers (not shown), for instance personal computers of operators, can log into the processor 1227 via the communications network 1272.

The processor 1227 may be implemented as an independent system or as a number of processing units that operate in parallel, wherein each processing unit is arranged to execute sub-tasks of a larger program. The processing units may also be divided in one or more main processing units with several sub-processing units. Some processing units of the processor 1227 may even be located a distance away of the other processing units and communicate via communications network 1272. Connections between modules can be made wired or wireless.

The computer system can be any signal processing system with analogue and/or digital and/or software technology arranged to perform the functions discussed here.

Although specific reference may have been made above to the use of embodiments of the invention in the context of optical lithography, it will be appreciated that the invention may be used in other applications, for example imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

Electron beam lithography is particularly of interest, as it is often used in the lithographic manufacturing process that creates the reticles used as patterning devices in the lithographic process of FIG. 2. The pattern on the reticle is produced by direct writing using a scanning electron beam. The techniques presented in the present disclosure can be applied in the analysis of defects and their causes in a lithographic process for the manufacture of reticles, just the same as in a process for the manufacture of functional devices using those reticles. The manufacturing process is substantially the same as that illustrated in FIG. 2, except that the pattern on the substrate (reticle blank) is produced by direct writing using a scanning electron beam.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The invention comprises the embodiments as defined in the following clauses:

1. A diagnostic apparatus for use in relation to a lithographic process, the diagnostic apparatus comprising a data processing apparatus programmed to perform automatically the steps of:
   receiving first measurement data representing a distribution of local deviations of a characteristic of one or more substrates subjected to the lithographic process;
   receiving second measurement data, the second measurement data representing a distribution of defects observed either on one or more substrates subjected to the same lithographic process or on a patterning device from which a pattern is transferred to said substrates in a patterning step of the lithographic process;
   identifying a correlation between the distribution of defects represented in the second measurement data and the distribution of local deviations represented in the first measurement data; and
   generating diagnostic information relating to the lithographic process based on the identified correlation.
2. An apparatus as defined in clause 1 wherein the distribution of the first measurement data represents distribution of local deviations with a first spatial resolution and the second measurement data represents the distribution of defects with a second spatial resolution, the second spatial resolution being higher than the first spatial resolution.
3. An apparatus as defined in any preceding clause wherein the first measurement data is based on height map data representing local deviations of surface height as a characteristic of the substrate.
4. An apparatus as defined in clause 3 wherein the first measurement data is based on height map data measured by a patterning apparatus while the first substrate is loaded onto a substrate support in a patterning apparatus for a patterning step of said lithographic process.
5. An apparatus as defined in clause 3 or 4 wherein said first measurement data is based on at least first height map data and second height map data, the first and second height map data being measured with the substrate subjected to different clamping conditions on the substrate support.
6. An apparatus as defined in clause 5, wherein said different clamping conditions include different polarities of clamping voltage on an electrostatic substrate support.
7. An apparatus as defined in clause 5 or 6 wherein the first measurement data is obtained by comparing height map data measured from a first substrate with reference height map data,
8. An apparatus as defined in clause 7 wherein said reference height map data is data measured previously from one or more reference substrates.
9. An apparatus as defined in clause 7 wherein said reference height map data is produced at least in part by filtering the height map data measured from the first substrate.
10. An apparatus as defined in any preceding clause wherein the first measurement data is obtained by comparing: (i) first height map data measured from the first substrate with the first substrate subjected to first clamping conditions on a substrate support of the patterning apparatus; (ii) first reference height map data representing a substrate free of defects subjected to the same first clamping conditions, the reference substrate(s) being regarded as free of defects; (iii) second height map data measured from the first substrate with the first substrate subjected to second clamping conditions different from the first clamping force; and (iv) second reference height map data representing a substrate free of defects subjected to the same second clamping conditions.
11. An apparatus as defined in any of clauses 1 to 3 wherein the first measurement data includes data measured by a patterning apparatus from a substrate support after the first substrate has been removed from the substrate support after a patterning step.
12. An apparatus as defined in clause 11 wherein said first measurement data represents local deviations of electrostatic charging across the substrate support.
13. An apparatus as defined in any preceding clause wherein said second measurement data represents defects observed by an inspection tool directly inspecting a reverse side of the substrate.
14. An apparatus as defined in any preceding clause wherein said first measurement data represents local deviations in one or more performance parameters of patterns applied to the substrate in a patterning step of said lithographic process.
15. An apparatus as defined in clause 13 wherein said performance parameter is an overlay error, being a positional deviation between features applied in two or more distinct patterning steps of said lithographic process.
16. An apparatus as defined in any preceding clause wherein said processor is further provided with a database of defect fingerprints, each defect fingerprint representing a spatial distribution of defects associated with one or more specific handling operations in the lithographic process, and wherein the step of generating diagnostic information includes using the identified correlation to recognize which, if any, of the defect fingerprints matches a spatial distribution of defects observed in relevant portions of the second measurement data.

17. An apparatus as defined in clause 16 wherein the processor is arranged to recognize said fingerprints by reference to spatial frequencies in the distribution of distances between said defects.

18. An apparatus as defined in clause 16 or 17 wherein said processor is arranged
    to identify clusters of defect points in the second measurement data
    to identify as relevant clusters those clusters which are present in portions of the second measurement data indicated by the identified correlation, and
    to use the clusters identified as relevant in recognizing the defect fingerprint.

19. An apparatus as defined in any preceding clause wherein the processor is arranged to identify said correlation by:
    deriving from the first measurement data a deviation map representing a distribution of local deviations in multiple regions distributed spatially across the substrate; and
    deriving from the second measurement data a defect map representing a density of defects observed in regions corresponding in spatial distribution with the regions of the deviation map; and
    identifying regions where the density of defects in the defect map is correlated with the density of local deviations in the deviation map.

20. An apparatus as defined in clause 19 wherein said defect density maps and resulting correlations are created for different defect size intervals.

21. An apparatus as defined in clause 19 or 20 wherein said measurement maps are subjected to weighting functions in order to normalize the data to specific values as a function of customizable thresholds.

22. An apparatus as defined in any preceding clause adapted for use where said lithographic process includes performing one or more of said processing steps by different individual processing apparatuses on different individual substrates, and wherein the processor is arranged to use context data identifying which of the individual processing apparatus has been used for a given processing step on the first substrate.

23. A lithographic processing system comprising one or more lithographic patterning apparatuses and one or more other processing apparatuses with associated substrate handling apparatuses, the lithographic system further comprising a diagnostic apparatus as defined in any preceding clause.

24. A lithographic processing system as defined in clause 23 wherein the diagnostic information identifies a specific one of said handling apparatuses as a suspected cause of said local deviations.

25. A lithographic processing system as defined in clause 23 or 24 further including a substrate backside inspection apparatus as a source of said second measurement data.

26. A lithographic processing system as defined in clause 23 or 24 further including a reticle backside inspection apparatus as a source of said second measurement data.

27. A lithographic processing system as defined in clause 23, 24, or 25 wherein said diagnostic apparatus is arranged to communicate with a control system of the lithographic processing system such that maintenance actions are controlled at least partly on the basis of the diagnostic information.

28. A computer program product or other non-transient memory device, having stored there on software that when run on a computer causes the computer to carry out the steps of: receiving first measurement data representing a distribution of local deviations of a characteristic of one or more substrates subjected to the lithographic process; receiving second measurement data, the second measurement data representing a distribution of defects observed either on one or more substrates subjected to the same lithographic process or on a patterning device from which a pattern is transferred to said substrates in a patterning step of the lithographic process; identifying a correlation between the distribution of defects represented in the second measurement data and the distribution of local deviations represented in the first measurement data; and generating diagnostic information relating to the lithographic process based on the identified correlation.

The breadth and scope of the present invention should not be limited by any of the above-described exemplary embodiments, but should be defined only in accordance with the following claims and their equivalents.

The invention claimed is:

1. A diagnostic apparatus for use in relation to a lithographic process, the diagnostic apparatus comprising a data processing apparatus programmed to automatically:
   receive first measurement data representing a distribution of local deviations of a characteristic associated with an interaction of one or more substrates with a substrate support;
   receive second measurement data, the second measurement data representing a distribution of defects observed either on one or more substrates subjected to the same lithographic process or on a patterning device from which a pattern is transferred to one or more substrates in a patterning step of the lithographic process, the second measurement data being of a different data type than the first measurement data;
   identify a correlation between the distribution of defects represented in the second measurement data and the distribution of local deviations represented in the first measurement data; and
   generate diagnostic information relating to the lithographic process based on the identified correlation.

2. The apparatus as claimed in claim 1, wherein the distribution of the first measurement data represents a distribution of local deviations with a first spatial resolution and the second measurement data represents a distribution of defects with a second spatial resolution, the second spatial resolution being higher than the first spatial resolution.

3. The apparatus as claimed in claim 1, wherein the first measurement data is based on height map data representing local deviations of surface height as the characteristic of the one or more substrates.

4. The apparatus as claimed in claim 3, wherein the first measurement data is based on height map data measured by a patterning apparatus while the one or more substrates are on, or loaded onto, a substrate support in the patterning apparatus for a patterning step of the lithographic process.

5. The apparatus as claimed in claim 3, wherein the first measurement data is based on at least first height map data and second height map data, the first and second height map data being measured with the one or more substrates subjected to different clamping conditions on the substrate support.

6. The apparatus as claimed in claim 5, wherein the first measurement data is obtained by comparing height map data measured from a first substrate with reference height map data.

7. The apparatus as claimed in claim 6, wherein the reference height map data is data measured previously from one or more reference substrates.

8. The apparatus as claimed in claim 1, wherein the first measurement data is obtained by comparing: (i) first height map data measured from a first substrate with the first substrate subjected to first clamping conditions on a substrate support of the patterning apparatus; (ii) first reference height map data representing a substrate free of defects subjected to the same first clamping conditions; (iii) second height map data measured from the first substrate with the first substrate subjected to second clamping conditions different from the first clamping conditions; and (iv) second reference height map data representing a substrate free of defects subjected to the same second clamping conditions.

9. The apparatus as claimed in claim 1, wherein the first measurement data includes data measured by a patterning apparatus from a substrate support after the one or more substrates have been removed from the substrate support after a patterning step.

10. The apparatus as claimed in claim 9, wherein the first measurement data represents local deviations of electrostatic charging across the substrate support.

11. The apparatus as claimed in claim 1, wherein the second measurement data represents defects observed by an inspection tool directly inspecting a reverse side of the one or more substrates.

12. The apparatus as claimed in claim 11, wherein the performance parameter is an overlay error, being a positional deviation between features applied in two or more distinct patterning steps of the lithographic process.

13. The apparatus as claimed in claim 1, wherein the first measurement data represents local deviations in one or more performance parameters of patterns applied to the one or more substrates in a patterning step of the lithographic process.

14. The apparatus as claimed in claim 1, wherein the data processing apparatus is further provided with a database of defect fingerprints, each defect fingerprint representing a spatial distribution of defects associated with one or more specific handling operations in the lithographic process, and wherein the generation of diagnostic information includes using the identified correlation to recognize which, if any, of the defect fingerprints matches a spatial distribution of defects observed in relevant portions of the second measurement data.

15. The apparatus as claimed in claim 14, wherein the data processing apparatus is arranged to recognize the fingerprints by reference to spatial frequencies in the distribution of distances between the defects.

16. The apparatus as claimed in claim 1, adapted for use where the lithographic process includes performing one or more of the processing steps by different individual processing apparatuses on different individual substrates, and wherein the data processing apparatus is arranged to use context data identifying which of the individual processing apparatuses has been used for a given processing step on the one or more substrates.

17. A lithographic processing system comprising one or more lithographic patterning apparatuses and one or more other processing apparatuses with one or more associated substrate handling apparatuses, the lithographic processing system further comprising the diagnostic apparatus as claimed in claim 1.

18. The lithographic processing system as claimed in claim 17, further comprising a substrate backside inspection apparatus and/or a patterning device backside inspection apparatus, as a source of the second measurement data.

19. The lithographic processing system as claimed in claim 17, wherein the diagnostic apparatus is arranged to communicate with a control system of the lithographic processing system such that maintenance actions are controlled at least partly on the basis of the diagnostic information.

20. A non-transitory computer program product having stored there on software that when run on a computer causes the computer at least:
receive first measurement data representing a distribution of local deviations of a characteristic associated with an interaction of one or more substrates with a substrate support;
receive second measurement data, the second measurement data representing a distribution of defects observed either on one or more substrates subjected to the same lithographic process or on a patterning device from which a pattern is transferred to one or more substrates in a patterning step of the lithographic process, the second measurement data being of a different data type than the first measurement data;
identify a correlation between the distribution of defects represented in the second measurement data and the distribution of local deviations represented in the first measurement data; and
generate diagnostic information relating to the lithographic process based on the identified correlation.

* * * * *